United States Patent
Chu

Patent Number: 5,814,420
Date of Patent: Sep. 29, 1998

[54] RECHARGEABLE POSITIVE ELECTRODES

[75] Inventor: May-Ying Chu, Oakland, Calif.

[73] Assignee: PolyPlus Battery Company, Inc., Berkeley, Calif.

[21] Appl. No.: 948,892

[22] Filed: Oct. 10, 1997

Related U.S. Application Data

[63] Continuation-in-part of Ser. No. 686,609, Jul. 26, 1996, Pat. No. 5,686,201, which is a continuation-in-part of Ser. No. 479,687, Jun. 7, 1995, Pat. No. 5,582,623, which is a continuation-in-part of Ser. No. 344,384, Nov. 23, 1994, Pat. No. 5,523,179.

[51] Int. Cl.$^6$ ...................................................... H01M 4/36
[52] U.S. Cl. ........................ 429/104; 429/102; 429/103; 429/190; 429/192; 429/194; 429/212; 429/213; 429/218; 429/233; 136/238; 136/263
[58] Field of Search .................................... 429/102, 103, 429/104, 190, 192, 194, 212, 213, 218, 233; 136/238, 263

[56] References Cited

U.S. PATENT DOCUMENTS

| | | | |
|---|---|---|---|
| 3,404,035 | 10/1968 | Kummer et al. | 136/6 |
| 3,413,150 | 11/1968 | Kummer et al. | 136/6 |
| 3,532,543 | 10/1970 | Nole et al. | 136/6 |
| 3,907,591 | 9/1975 | Lauck | 136/6 |
| 3,915,743 | 10/1975 | Lauck | 136/6 |
| 3,953,231 | 4/1976 | Farrington et al. | 136/6 |
| 4,143,214 | 3/1979 | Chang | 429/112 |
| 4,268,587 | 5/1981 | Farrington et al. | 429/193 |
| 4,410,609 | 10/1983 | Peled et al. | 429/105 |
| 4,469,761 | 9/1984 | Bennett et al. | 429/50 |
| 4,644,911 | 2/1987 | Perichaud et al. | 429/194 |
| 4,833,048 | 5/1989 | Dejonghe et al. | 429/104 |
| 4,917,974 | 4/1990 | De Jonghe et al. | 429/104 |
| 5,162,175 | 11/1992 | Visco et al. | 429/192 |
| 5,523,179 | 6/1996 | Chu | 429/104 |
| 5,529,860 | 6/1996 | Skotheim et al. | 429/213 |
| 5,532,077 | 7/1996 | Chu | 429/102 |
| 5,582,623 | 12/1996 | Chu | 429/192 |
| 5,686,201 | 11/1997 | Chu | 429/192 |

FOREIGN PATENT DOCUMENTS

| | | |
|---|---|---|
| 0602984A2 | 6/1994 | European Pat. Off. . |
| 6-275313 | 9/1994 | Japan . |
| 2 273 603 | 10/1984 | United Kingdom . |
| 2 137406 | 6/1994 | United Kingdom . |

OTHER PUBLICATIONS

Abstract of proceedings of the 6th International Symposium on Power Sources 2, 1968, Brighton, Sussex, UK 24–26, Sep. 1968.

Coleman et al., "The Sulfur Electrode" proceedings of the 6th International Symposium on Power sources, pp. 289–302 (1968). No month available.

Visco, S.J., Liu, M., Armand, B. and De Jonghe, L.C., Solid Redox Polymerization Electrodes and Their use in All–Solid–State Batteries, Mol. Cryst. Liq. Cryst., 190, p. 198, 1990. No month available.

(List continued on next page.)

*Primary Examiner*—Bruce F. Bell
*Attorney, Agent, or Firm*—Beyer & Weaver, LLP

[57] ABSTRACT

Disclosed are positive electrodes containing active-sulfur-based composite electrodes. The cells include active-sulfur, an electronic conductor, and an ionic conductor. These materials are provided in a manner allowing at least about 10% of the active-sulfur to be available for electrochemical reaction. Also disclosed are methods for fabricating active-sulfur-based composite electrodes. The method begins with a step of combining the electrode components in a slurry. Next, the slurry is homogenized such that the electrode components are well mixed and free of agglomerates. Thereafter, before the electrode components have settled or separated to any significant degree, the slurry is coated on a substrate to form a thin film. Finally, the coated film is dried to form the electrode in such a manner that the electrode components do not significantly redistribute.

28 Claims, 13 Drawing Sheets

Schematic of a Li/electrolyte separator/active –sulfur electrode cell

OTHER PUBLICATIONS

Societe des Accumulateurs Fixes et de Traction, "Lithium–sulfur battery" Abstracts 111055d, Chemical Abstracts 66: 10360; 1967. No month available.

DeGott, P., "Polymere Carbone–Soufre Synthese Et Proprietes Electrochimiques," Doctoral Thesis at l'Institut National Polytechnique de Grenoble, (Date of Defense 19 Jun. 1986).

Lauck, H., "Storage battery with lithium anode and sulfur cathode," Abstract #9855s, Chemical Abstracts, 80: 467–468; 1974. No month available.

Peled et al., Rechargeable Lithium–Sulfur Battery (Extended Abstact), Journal of Power Source, 26: 269–271, 1989. No month available.

Peled et al.; "Lithium–Sulfur Battery: Evaluation of Dioxolane–Based Electrolytes", J. Electrochem., Soc., 136(6): 1621–1624, Jun. 1989.

Peramunage and Licht, "A Solid Sulfur Cathode for Aqueous Batteries"; Science 261: 1029–1032, Aug. 20, 1993.

Rauh et al., "Formation of Lithium Polysulfides in Aprotic Media", J. Inorg., Nuc. Chem., 39: 1761–1765, 1977. No month available.

Rauh et al. "A Lithium/Dissolved Sulfur Battery with an Organic Electrolyte"; J. Electrochem. Soc., 126(4): 523–527, Apr. 1979.

Yamin and Peled, "Electrochemistry of Nonaqueous Lithium/Sulfur Cell", J. Power Sources, 9: 281–287, 1983. No month available.

Yamin et al., Lithium Sulfur Battery,: J. Electrochem. Soc., 135(5): 1045–1048, May 1988.

S.J. Visco, M.M. Doeff, and L.C. De Jonghe, "Thin–Film Technology for Solid–State Lithium Batteries Employing Solid Redox Poly–Merization Cathodes", pp. 89–92, Society of Vacuum Coaters, 1991. No month available.

Liu, Meilin, Visco, Steven J., and De Jonghe, Lutgard C., "Novel Solid Redox Polymerization Electrodes Electrochemical Properties", J. Electrochem Soc., vol. 138, No. 7, pp. 1896–1901, Jul. 1991.

Liu, Meilin, Visco, Steven J., and De Jonghe, Lutgard C., "Novel Solid Redox Polymerization Electrodes All–Solid State, Thin–Film, Rechargeable Lithium Batteries", J. Electrochem Soc., vol. 138, No. 7, pp. 1891–1895, Jul. 1991.

Ue, Makoto, Visco, Steven J., and De Jonghe, Lutgard C., "Comparison of Cathode Utilization between Polymeric Organodisulfide and Titanium Disulfide in Solid Polymer Electrode Rechargeable Lithium Cells", Denki Kagaku, vol. 61, No. 12, pp. 1409–1415, 1993. No month available.

Meilin, Lui, "Novel Electrodes for Advanced Energy Storage System" Dissertation for Ph.D. at the University of Berkeley, Chapter 2, pp. 3–6, 1989. No month available.

J.R. Coleman, et al., "The Sulfur Electrode", (1968) 289–302, Defense Chemical Biological and Radiation Establishment, Defense Research Board, Ottawa, Canada. No month available.

R.D. Rauh, et al., Rechargeability Studies of Ambient Temperature Lithium/Sulfur Batteries, EIC Corporation, 55 Chapel Street, Newton, MA 02158. No month/year available.

D. Nole, et al., "Battery Employing Lithium–Sulphur Electrodes with Non–Aqueous Electrolyte", U.S. Patent 3,532,543 (1970). No month available.

E. Peled, et al. "Lithium–Sulfur Battery: Evaluation of Dioxolane Based Electrodes", J. Electrochemical Society, 136, 1621–1624 (1989). No month available.

A. Yamin, et al. "Electrochemistry of a Nonaqueous Lithium/Sulfur Cell", J. Power Sources, 9, 281–287 (1983). No month available.

H. Yamin, et al. "Lithium Sulfur Battery–Oxidation/Reduction Mechanisms of Polysulfides in THF Solutions", J. Electrochemical Society, 135, 1045–104 (1988). No month available.

S.B. Brummer, et al. "Low Temperature Lithium/Sulfur Secondary Battery", U.S. Energy Research and Development Administration Div. of Electric Energy Systems, 1–57 (1976). No month available.

E. Peled, et al. "Rechargeable Lithium–Sulfur Battery (Extended Abstract)", J. Power Sources, 26, 269–271 (1989). No month available.

Peled, et al. "Electrochemical Cell", U.S. Patent 4,410,609 (1983). No month available.

R.D. Rauh, et al. "Formation of Lithium Polysulfides in Aprotic Media", J. Inorg. Nuc. Chem., 39, 1761–1765 (1977). No month available.

R.D. Rauh, et al. "A Lithium/Dissolved Sulfur Battery with an Organic Electrolyte", J. Electrochemical Society, 126, 523–527 (1979). No month available.

R.D. Rauh, et al. "Rechargeability Studies of Ambient Temperature Lithium/Sulfur Batteries", 12th IECEC, 283–287 (1977). No month available.

A. Gavrilov, et al., "In Situ Morphological Study of Lithium–Electrolyte Interface", Electrochemical Society, (Extended Abstract). No month/year available.

Kavan, L., Novak, P., and Dousek, F.P., "Electrochimica Acto," vol. 33, No. 11, pp. 1605–1612, Mar. 8, 1988, Great Britain.

Brummer, S.B., et al., "Low Temperature Lithium/Sulfur Secondary Battery (Annual Progress Report, Dec. 1, 1974–Dec. 1, 1975)", EIC Corporation, Apr. 1976, Newton, Massachusetts.

Larry A. Dominey, "Lithium Batteries" New Material, Developments and Perspectives, 1994, New York, Industrial Chemistry Library, vol. 5, pp. 137–165. No month available.

Ronald Snaith, et al., "Lithium Chemistry" A Theoretical and Experimental Overview, 1995, New York, John Wiley & Sons, Inc., pp. 227–477. No month available.

Schematic of a Li/electrolyte separator/active-sulfur electrode cell

End of discharge voltage vs. number of recharge cycles
(330 mAh/gm of active-sulfur, 30°C)

Voltage vs. mAh/gm of active-sulfur for first discharge (30°)

Voltage vs. mAh/gm of active-sulfur for first discharge (30°c, gel-state elecrolyte separator)

Voltage vs. mAh/gm of active-sulfur for first discharge (90°C)

End of discharge voltage vs. number of recharge cycles
(400 mAh/gm active-sulfur, 90°C)

mAh/gm of active-sulfur vs. number of recharge cycles (90°C)

Specific power of the positive electrode vs. current density (90°C)

TABLE 1

| | Temp, Type | Result based on Cathode Film Performance* | # Cycles | Battery Projections** | Battery Projections*** |
|---|---|---|---|---|---|
| 1 | 30°C, solid-state | 880 Wh/kg | N.A. | 440 Wh/kg | 550 Wh/l |
| 2 | 30°C, solid-state | 300 Wh/kg | 50+ | 150 Wh/kg | 190 Wh/l |
| 3 | 30°C, gel-state component | 980 Wh/kg | N.A. | 490 Wh/kg | 610 Wh/l |
| 4 | 90°C, solid-state | 1500 Wh/kg | N.A. | 630 Wh/kg | 790 Wh/l |
| 5 | 90°C, solid-state | 400 Wh/kg | 30+ | 200 Wh/kg | 250 Wh/l |
| 6 | 90°C, solid-state | 1000 Wh/kg | ~10 | 500 Wh/kg | 630 Wh/l |
| 7 | 90°C, solid-state | max: 3000 W/kg | N.A. | 1500 W/kg | 1880 W/l |

\*    Mean voltage 2.0V.
\*\*    Assumed battery burden of 100%.
\*\*\*    Battery density approximately 1.25 gm/cm$^3$

Figure 12a

TABLE 2

| Temp, Type | Result based on Cathode Film Performance * | Result based on Cathode Film Performance * | # of Cycles | Battery Projections ** | Battery Projections ** |
|---|---|---|---|---|---|
| 90°C, solid-state | 200 Wh/kg | 715 W/kg | 400 | 100 Wh/kg | 360 Wh/l |
| 90°C, solid-state | 300 Wh/kg | 815 W/kg | 280 | 150 Wh/kg | 410 Wh/l |
| 90°C, solid-state | 400 Wh/kg | 810 W/kg | 160 | 200 Wh/kg | 405 Wh/l |
| 90°C, solid-state | 600 Wh/kg | 615 W/kg | 55 | 300 Wh/kg | 310 Wh/l |
| 90°C, solid-state | >800 Wh/kg | 420 W/kg | 50 | >400 Wh/kg | 210 Wh/l |
| 90°C, solid-state | >1000 Wh/kg | 330 W/kg | 20 | >500 Wh/kg | 165 Wh/l |
| 70°C, solid-state | 1220 Wh/kg | 120 W/kg | N.A. | 610 Wh/kg | 60 W/kg |
| 90°C, solid-state Peak Power | 7400 W/kg @20 wh/kg | N.A. | N.A. | 3700 W/kg | N.A. |

\* Mean voltage 2.0V.

\*\* Assumed battery burden of 100%, battery density approximately 1.25 gm/cm$^3$

Figure 12b

Specific power of the positive electrode vs. current density (90°C)

RECHARGEABLE POSITIVE ELECTRODES

CROSS-REFERENCE TO RELATED APPLICATIONS

This application is a continuation-in-part of U.S. patent application Ser. No. 08/686,609, filed Jul. 26, 1996 (now U.S. Pat. No. 5,686,201), and entitled RECHARGEABLE POSITIVE ELECTRODES, which is a continuation-in-part of U.S. patent application Ser. No. 08/479,687 (now U.S. Pat. No. 5,582,623, issued Dec. 10, 1996, filed Jun. 7, 1995, and entitled METHODS OF FABRICATING RECHARGEABLE POSITIVE ELECTRODES) which is, in turn, a continuation-in-part of U.S. patent application Ser. No. 08/344,384 (now U.S. Pat. No. 5,523,179, issued Jun. 4, 1996, filed Nov. 23, 1994, and entitled RECHARGEABLE POSITIVE ELECTRODE). U.S. patent application Ser. No. 08/686,609 is incorporated herein by reference for all purposes. In addition, both U.S. Pat. Nos. 5,582,623 and 5,523,179 are incorporated herein by reference for all purposes.

BACKGROUND OF THE INVENTION

This invention relates generally to positive electrodes characterized by active-sulfur. The electrodes are preferably rechargeable, and in some preferred embodiments are constructed in a thin-film format. Various negative electrodes, such as, alkali metal, alkaline earth metal, transition metal, and carbon insertion electrodes, among others, can be coupled with the positive electrode to provide battery cells, preferably having high specific energy (Wh/kg) and energy density (Wh/l).

The rapid proliferation of portable electronic devices in the international marketplace has led to a corresponding increase in the demand for advanced secondary batteries. The miniaturization of such devices as, for example, cellular phones, laptop computers, etc., has naturally fueled the desire for rechargeable batteries having high specific energies (light weight). At the same time, mounting concerns regarding the environmental impact of throwaway technologies, has caused a discernible shift away from primary batteries and towards rechargeable systems.

In addition, heightened awareness concerning toxic waste has motivated, in part, efforts to replace toxic cadmium electrodes in nickel/cadmium batteries with the more benign hydrogen storage electrodes in nickel/metal hydride cells. For the above reasons, there is a strong market potential for environmentally benign secondary battery technologies.

Secondary batteries are in widespread use in modern society, particularly in applications where large amounts of energy are not required. However, it is desirable to use batteries in applications requiring considerable power, and much effort has been expended in developing batteries suitable for high specific energy, medium power applications, such as, for electric vehicles and load leveling. Of course, such batteries are also suitable for use in lower power applications such as cameras or portable recording devices.

At this time, the most common secondary batteries are probably the lead-acid batteries used in automobiles. Those batteries have the advantage of being capable of operating for many charge cycles without significant loss of performance. However, such batteries have a low energy to weight ratio. Similar limitations are found in most other systems, such as Ni-Cd and nickel metal hydride systems.

Among the factors leading to the successful development of high specific energy batteries, is the fundamental need for high cell voltage and low equivalent weight electrode materials. Electrode materials must also fulfill the basic electrochemical requirements of sufficient electronic and ionic conductivity, high reversibility of the oxidation/reduction reaction, as well as excellent thermal and chemical stability within the temperature range for a particular application. Importantly, the electrode materials must be reasonably inexpensive, widely available, non-toxic, and easy to process.

Thus, a smaller, lighter, cheaper, non-toxic battery is sought for the next generation of batteries. The low equivalent weight of lithium renders it attractive as a battery electrode component for improving weight ratios. Lithium provides also greater energy per volume than do the traditional battery standards, nickel and cadmium.

The low equivalent weight and low cost of sulfur and its nontoxicity renders it also an attractive candidate battery component. Successful lithium/organosulfur battery cells are known. (See, De Jonghe et al., U.S. Pat. Nos. 4,833,048 and 4,917,974; and Visco et al., U.S. Pat. No. 5,162,175.)

However, employing a positive electrode based on elemental sulfur in an alkali metal-sulfur battery system has been considered problematic. Although theoretically the reduction of sulfur to an alkali metal sulfide confers a large specific energy, sulfur is known to be an excellent insulator, and problems using it as an electrode have been noted. Such problems referred to by those in the art include the necessity of adjoining the sulfur to an inert electronic conductor, very low percentages of utilization of the bulk material, poor reversibility, and the formation of an insulating sulfur film on the carbon particles (used to impart electronic conductivity to the sulfur electrode) and current collector surface that electronically isolates the rest of the electrode components. (DeGott, P., "Polymere Carbone-Soufre Synthèse et Propriétes Electrochimiques," Doctoral Thesis at the Institut National Polytechnique de Grenoble (date of defense of thesis: 19 Jun., 1986) at page 117.)

Similarly, Rauh et al., "A Lithium/Dissolved Sulfur Battery with an Organic Electrolyte," *J. Electrochem. Soc.*, 126 (4): 523 (April 1979) state at page 523: "Both $S_8$ and its ultimate discharge product, $Li_2S$, are electrical insulators. Thus it is likely that insulation of the positive electrode material . . . led to the poor results for Li/S cells."

Further, Peramunage and Licht, "A Solid Sulfur Cathode for Aqueous Batteries," *Science*, 261: 1029 (20 Aug. 1993) state at page 1030: "At low (room) temperatures, elemental sulfur is a highly insoluble, insulating solid and is not expected to be a useful positive electrode material." However, Peramunage and Licht found that interfacing sulfur with an aqueous sulfur-saturated polysulfide solution converts it from an insulator to an ionic conductor.

The use of sulfur and/or polysulfide electrodes in nonaqueous or aqueous liquid-electrolyte lithium batteries (that is, in liquid formats) is known. For example, Peled and Yamin, U.S. Pat. No. 4,410,609, describe the use of a polysulfide positive electrode $Li_2S_x$ made by the direct reaction of Li and S in tetrahydrofuran (THF). Poor cycling efficiency typically occurs in such a cell because of the use of a liquid electrolyte with lithium metal foil, and the Peled and Yamin patent describes the system for primary batteries. Rauh et al., "Rechargeable Lithium-Sulfur Battery (Extended Abstract), *J. Power Sources*, 26: 269 (1989) also notes the poor cycling efficiency of such cells and states at page 270 that "most cells failed as a result of lithium depletion."

Other references to lithium-sulfur battery systems in liquid formats include the following: Yamin et al., "Lithium Sulfur Battery," *J. Electrochem. Soc.*, 135(5): 1045 (May 1988); Yamin and Peled, "Electrochemistry of a Nonaqueous Lithium/Sulfur Cell," *J. Power Sources*, 9: 281 (1983); Peled et al., "Lithium-Sulfur Battery: Evaluation of Dioxolane-Based Electrolytes," *J. Electrochem, Soc.*, 136 (6): 1621 (Jun. 1989); Bennett et al., U.S. Pat. No. 4,469,761; Farrington and Roth, U.S. Pat. No. 3,953,231; Nole and Moss, U.S. Pat. No. 3,532,543; Lauck, H., U.S. Pat. Nos. 3,915,743 and 3,907,591; Societe des Accumulateurs Fixes et de Traction, "Lithium-sulfur battery," *Chem. Abstracts*, 66: Abstract No. 111055d at page 10360 (1967); and Lauck, H. "Electric storage battery with negative lithium electrode and positive sulfur electrode," *Chem. Abstracts*, 80: Abstract No. 9855 at pages 466–467 (1974).)

High temperature molten sodium-sulfur cells are known and described in U.S. Pat. No. 3,413,150 issued to Kummer et al. on Nov. 26, 1968 and U.S. Pat. No. 3,404,035 issued to Kummer et al. on Oct. 1, 1968 Such cells employ a solid state separator, typically a ceramic such as an alumina. Obviously such cells must be operated at a temperature above the melting point of sodium. A lower temperature version of such cells has been proposed in U.S. Pat. No. 4,268,587 issued to Farrington et al. on May 19, 1981. In that patent, the described cell employed a ceramic separator as in the high temperature version. It also employed a positive electrode including elemental sulfur, an electronic conductor (e.g., carbon) and a "drop" of liquid ionic conductor.

DeGott, supra, notes at page 118 that alkali metal-sulfur battery systems have been studied in different formats, and then presents the problems with each of the studied formats. For example, he notes that an "all liquid" system had been rapidly abandoned for a number of reasons including among others, problems of corrosiveness of liquid lithium and sulfur, of lithium dissolving into the electrolyte provoking self-discharge of the system, and that lithium sulfide forming in the positive (electrode) reacts with the sulfur to give polysulfides $Li_2S_x$ that are soluble in the electrolyte.

In regard to alkali metal-sulfur systems wherein the electrodes are molten or dissolved, and the electrolyte is solid, which function in exemplary temperature ranges of 130° C. to 180° C. and 300° C. to 350° C., DeGott states at page 118 that such batteries have problems, such as, progressive diminution of the cell's capacity, appearance of electronic conductivity in the electrolyte, and problems of safety and corrosion. DeGott then lists problems encountered with alkali metal-sulfur battery systems wherein the electrodes are solid and the electrolyte is an organic liquid, and by extension wherein the negative electrode is solid, the electrolyte is solid, and the positive electrode is liquid. Such problems include incomplete reduction of sulfur, mediocre reversibility, weak maximum specific power (performance limited to slow discharge regimes), destruction of the passivating layer of $Li_2S$ as a result of its reaction with dissolved sulfur leading to the formation of soluble polysulfides, and problems with the stability of the solvent in the presence of lithium.

DeGott also describes on page 117 a fundamental barrier to good reversibility as follows. As alkali metal sulfides are ionic conductors, they permit, to the degree that a current collector is adjacent to sulfur, the propagation of a reduction reaction. By contrast, their reoxidation leads to the formation of an insulating sulfur layer on the positive electrode that ionically insulates the rest of the composite, resulting in poor reversibility.

DeGott concludes on page 119 that it is clear that whatever format is adopted for an alkali metal-sulfur battery system that the insulating character of sulfur is a major obstacle that is difficult to overcome. He then describes preliminary electrochemical experiments with a composite sulfur electrode prepared from a slurry. The slurry was prepared by mixing the following components in acetonitrile: 46% sulfur; 16% acetylene black; and 38% $(PEO)_8/LiClO_4$ (polyethylene oxide/lithium perchlorate). The resulting slurry was then deposited on a stainless steel substrate by "capillary action." From those preliminary experiments, DeGott concludes on page 128 that it is clear that, even when optimizing the efficiency of the composite electrode (that is, by multiplying the triple point contacts) that elemental sulfur cannot be considered to constitute an electrode for a secondary battery, in an "all solid" format.

Present solid-state lithium secondary battery systems are limited to a specific energy of about 120 Wh/kg. It would be highly desirable to have a battery system characterized by higher specific energy values.

It would be even more desirable if solid-state batteries having practical specific energy values greater than about 150 Wh/kg could operate at room temperature. It would be additionally advantageous if solid-state batteries having high specific energy and operation at room temperature could be reliably fabricated into units with reproducible performance values.

In lithium cells wherein a liquid electrolyte is used, leakage of the electrolyte can leave lithium exposed to the air, where it rapidly reacts with water vapor and oxygen. Substantial casing can prevent such reactions and protect users and the environment from exposure to hazardous, corrosive, flammable or toxic solvents but adds unwanted weight to the battery. A solid-state battery would greatly reduce such problems of electrolyte leakage and exposure of lithium, and would allow reducing the weight of the battery.

Furthermore, a battery formulation that overcomes the problem of lithium depletion described in the prior art, for example, Rauh et al., supra, would have many advantages.

In summary, disadvantages in currently available metal-sulfur battery systems include poor cycling efficiency, poor reversibility, lithium depletion, or operating temperatures above 200° C., among other problems. Practitioners in the battery art have long sought a solid-state or gel-state metal-sulfur battery system that would overcome these limitations.

SUMMARY OF THE INVENTION

In one aspect, the present invention provides a battery cell that may be characterized as including the following elements: (a) a negative electrode including a metal or an ion of the metal; (b) a sulfur positive electrode; and (c) a gel-state or polymeric solid-state electrolyte separator electronically separating the positive and negative electrodes. The positive electrode includes (i) an electrochemically active material including sulfur in the form of at least one of elemental sulfur, a sulfide of the metal, and a polysulfide of the metal, and (ii) an electronically conductive material. In addition, the positive electrode should exist in a state in which at least about 10% of the sulfur is accessible to electrons and ionic charge carriers.

Preferably, the positive electrode also includes a liquid-state ionic conductor. Examples of such liquid-state ionic conductor include sulfolane, dimethyl sulfone, a dialkyl carbonate, tetrahydrofuran, dioxolane, propylene carbonate, ethylene carbonate, dimethyl carbonate, butyrolactone, N-methylpyrrolidinone, tetramethylurea, glymes, ethers, a crown ether, and dimethoxyethane.

The battery cells of this invention may be rechargeable. If so, they should preferably meet certain performance criteria.

For example, a battery cell of this invention preferably has at least about 10% of the sulfur in the positive electrode accessible to electrons and ionic charge carriers over at least about 50 successive cycles. Alternatively, at least about 50% of the sulfur should be accessible to electrons and ionic charge carriers that over at least about 2 successive cycles.

The electronic conductor of the positive electrode may be carbon or an electronically conductive polymer, for example. In a particularly preferred embodiment, the positive electrode includes an polymeric disulfide material in which the disulfide bond is located in the material's backbone.

If the electrolyte separator is a gel-state electrolyte separator, it will include at least about 20% by weight of an aprotic organic liquid immobilized by the presence of a gelling agent. Examples of such aprotic organic liquids include sulfolane, dimethyl sulfone, a dialkyl carbonate, tetrahydrofuran, dioxolane, propylene carbonate, ethylene carbonate, dimethyl carbonate, butyrolactone, N-methylpyrrolidinone, tetramethylurea, glymes, ethers, a crown ether, and dimethoxyethane. If the electrolyte separator is a solid-state electrolyte separator, it preferably a polymeric solid-state electrolyte separator such as a polymer of ethylene oxide.

These and other features of the invention will further described and exemplified in the drawings and detailed description below.

BRIEF DESCRIPTION OF THE DRAWINGS

FIG. 12a is a table illustrating the performance of the cells prepared and operated as described in examples 1–8.

FIG. 12b is a table illustrating the performance of the cells prepared and operated as described in examples 9–15.

FIG. 14b is a plot of the end of discharge voltage vs. number of recharge cycles for the cell of FIG. 14a.

DETAILED DESCRIPTION

Figure 1:
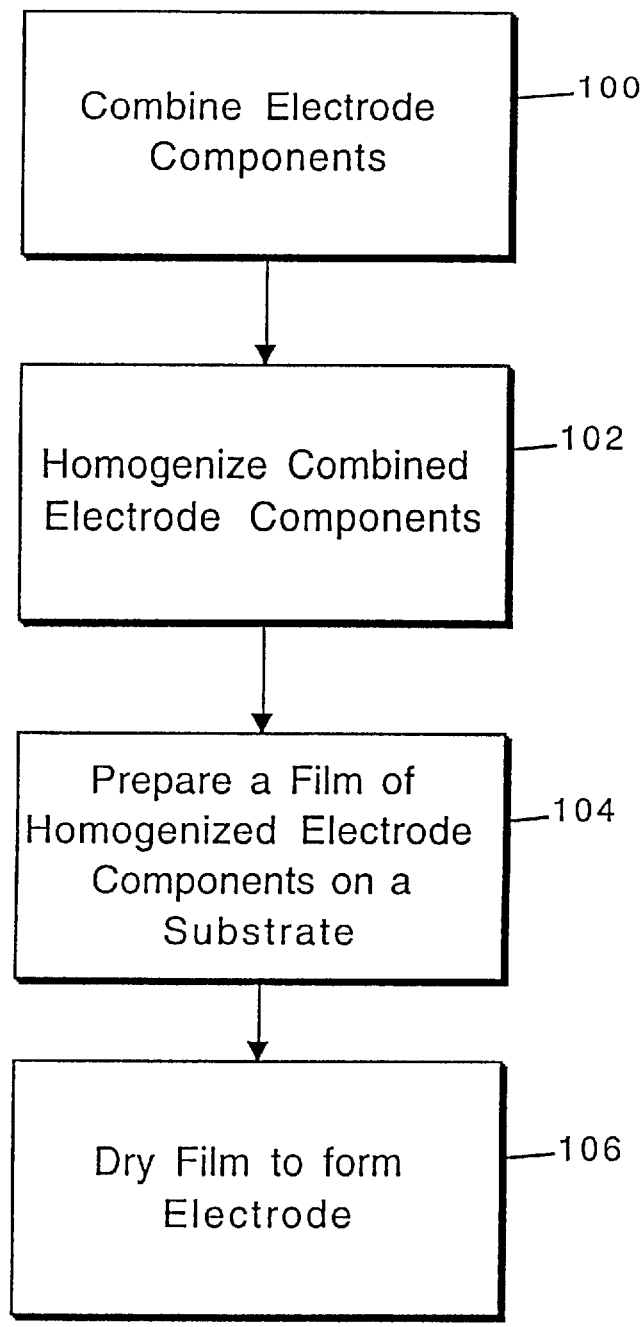
FIG. 1 provides a flow chart showing the important steps employed in preparing an electrode in accordance with this invention.

The term "active-sulfur" is defined herein to be elemental sulfur or sulfur that would be elemental if the positive electrode were in its theoretically fully charged state. Regardless of the initial state of the positive electrode, it contains active sulfur if at any time in a battery cycle, it includes elemental sulfur, a sulfide of the negative electrode metal, and/or polysulfides of the negative electrode metal.

The term "solid-state" is defined herein to be a material which contains less than 20% by weight of a liquid.

The term "gel-state" is defined herein to be a material containing at least 20% by weight of a liquid wherein said liquid is immobilized by the presence of a gelling agent.

The term "component" is defined herein to be (a) positive electrode, (b) electrolyte separator, or (c) negative electrode.

The instant invention provides a positive electrode for solid-state and liquid format battery systems, wherein the positive electrode is based on active-sulfur which provides high specific energy and power, exceeding that of highly developed systems now known and in use. Solid-state format battery cell means all the components of the battery are either solid-state or gel-state. It further means that no component is in a liquid-state. The equivalent weight of the active-sulfur used in the redox reactions within the battery cells of this invention is 16 grams/equivalent (with a lithium metal as the negative electrode, active-sulfur in its theoretically fully discharged state is $Li_2S$), leading to a theoretical specific energy of 2800 watthours per kilogram (Wh/kg) for a lithium cell having a average OCV of 2.4 volts. Such an exceedingly high specific energy is very unusual and highly attractive.

Further, the batteries containing the positive electrode of this invention can operate at room temperature. The battery systems of this invention provide energy to weight ratios far in excess of the present demands for load leveling and/or electric vehicle applications, and can be reliably fabricated into units with reproducible performance values.

This invention can be incorporated in a battery cell which includes solid-state or gel-electrolyte separators. This embodiment excludes the problem of a battery cell in the liquid format that may suffer electrolyte leakage. For example, in lithium cells wherein a liquid electrolyte is used, leakage of the electrolyte can leave lithium exposed to the air, where it rapidly reacts with water vapor. Substantive casing can prevent such reactions and protects users and the environment from exposure to solvents but adds unwanted weight to the battery. Using a solid-state or gel-state format battery cells greatly reduces such problems of electrolyte leakage and exposure of lithium, and can cut down on the weight of the battery.

Another embodiment concerns battery cells in a liquid format, which have a solid active-sulfur-based positive electrode of this invention, and which have a solid negative electrode that contains carbon (when in the fully discharged state), carbon inserted with lithium or sodium and/or a mixture of carbon with lithium or sodium. Such an embodiment can overcome the problem of lithium depletion described in the prior art, for example, Rauh et al., supra.

In accordance with this invention, the active-sulfur-based composite positive electrode and a battery system constructed with said positive electrode are provided. The positive electrodes of this invention are preferably reversible, and the metal-active-sulfur battery cells are preferably secondary batteries, and more preferably thin film secondary batteries.

The invention relates in one aspect to the positive electrode of battery cells wherein both the positive and negative electrodes are solid-state or gel-state and the electrolyte separator is either a solid-state or a gel-state material (see Definition). In another aspect, as indicated above, the positive electrode of this invention is used in a battery cell which contains a liquid electrolyte wherein the negative electrode is solid or gel-state and contains carbon, carbon inserted with lithium or sodium, or mixtures of carbon with lithium or sodium. However, whatever the format of the battery cells made with the positive electrodes of this invention, said positive electrode comprises elemental sulfur as the active component when in the theoretically fully charged state.

The positive electrode of this invention may be a composite including, in the theoretically fully charged state, elemental sulfur, preferably an ionically conductive material, and an electronically conductive material. Upon discharge, the active-sulfur of the positive electrode reacts with the metal of the negative electrode, and metal sulfides and polysulfides form. For example, where M is the metal of the negative electrode, the overall cell reaction can be described as follows:

$$x/zM + S = M_{x/z}S$$

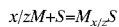

wherein M is any metal that can function as an active component in a negative electrode in a battery cell wherein active-sulfur is the active component of the positive electrode; x=0 through x=2; z=the valence of the metal; and S is sulfur.

M is preferably selected from the group consisting of alkali metals, alkaline earth metals, and transition metals. M is more preferably selected from the group consisting of alkali metals, and still more preferably lithium or sodium. M is most preferably lithium.

More specifically, for example, in a preferred embodiment of this invention wherein the negative electrode contains lithium, the overall cell reaction wherein z=1 can be described as follows:

$$xLi + S = Li_xS.$$

When x=2, 100% of the theoretical specific energy of the system has been released.

Upon discharge, the positive electrode becomes a combination of sulfur, metal sulfides and polysulfides, and during the discharging process the proportions of those sulfur-containing components will change according to the state of charge. The charge/discharge process in the positive electrode is reversible. Similarly, upon recharging, the percentages of the sulfur-containing ingredient will vary during the process.

The positive electrode is thus made from an electrode composition comprising active-sulfur, an electronically conductive material intermixed with the active-sulfur in a manner that permits electrons to move between the active-sulfur and the electronically conductive material, and an ionically conductive material intermixed with the active-sulfur in a manner that permits ions to move between the ionically conductive material and the sulfur.

The ionically conductive material of said composite positive electrode is preferably a polymeric electrolyte, more preferably a polyalkylene oxide, and further, preferably polyethylene oxide in which an appropriate salt may be added. Additional ionically conductive materials for use in the positive electrode include the components described below in the solid-state and gel-state electrolyte separator.

Exemplary electronically conductive materials of the composite positive electrode include carbon black, electronically conductive compounds with conjugated carbon-carbon and/or carbon-nitrogen double bonds, for example but not limited to, electronically conductive polymers, such as, polyaniline, polythiophene, polyacetylene, polypyrrole, and combinations of such electronically conductive materials. The electronically conductive materials of the positive electrode may also have electrocatalytic activity.

The composite sulfur-based positive electrode may further optionally comprise performance enhancing additives, such as, binders; electrocatalysts, for example, phthalocyanines, metallocenes, brilliant yellow (Reg. No. 3051-11-4 from Aldrich Catalog Handbook of Fine Chemicals; Aldrich Chemical Company, Inc., 1001 West Saint Paul Avenue, Milwaukee, Wis. 53233 (USA)) among other electrocatalysts; surfactants; dispersants (for example, to improve the homogeneity of the electrode's ingredients); and protective layer forming additives (for example, to protect a lithium negative electrode), such as, organosulfur compounds, phosphates, iodides, iodine, metal sulfides, nitrides, and fluorides, for example LiI, PbS, and HF.

The range of active-sulfur in such electrodes in the theoretically fully charged state is from 20% to 80% by weight. Said active-sulfur-based composite electrode is preferably processed such that the component particles are homogeneously distributed, and segregation and/or agglomeration of the component particles is avoided.

A metal-sulfur battery system constructed with said active-sulfur-based composite positive electrode of this invention should have at least 5%, and more preferably at least 10% availability of the active-sulfur. That availability corresponds to a minimum of 168 mAh per gram of sulfur included in the positive electrode. This is based on the theoretical value of 1675 mAh/gm of sulfur at 100% availability.

The electrolyte separator used in combination with the positive electrodes of this invention functions as a separator for the electrodes and as a transport medium for the metal ions. Any electronically insulating and ionically conductive material which is electrochemically stable may be used. For example, it has been shown that polymeric, glass and/or ceramic materials are appropriate as electrolyte separators, as well as other materials known to those of skill in the art, such as, porous membranes and composites of such materials. Preferably, however, the solid-state electrolyte separator is any suitable ceramic, glass, or polymer electrolyte such as, polyethers, polyimines, polythioethers, polyphosphazenes, polymer blends, and the like, in which an appropriate electrolyte salt may be added. In the solid-state, the electrolyte separator may contain an aprotic organic liquid wherein said liquid constitutes less than 20% (weight percentage) of the total weight of the electrolyte separator.

In the gel-state, the electrolyte separator contains at least 20% (weight percentage) of an aprotic organic liquid wherein the liquid is immobilized by the inclusion of a gelling agent. Any gelling agent, for example, polyacrylonitrile, PVDF, or PEO, can be used.

The liquid electrolyte for the liquid format batteries using the positive electrode of this invention, is also preferably an aprotic organic liquid. The liquid format battery cells constructed using the positive electrodes of this invention would preferably further comprise a separator which acts as an inert physical barrier within the liquid electrolyte. Exemplary of such separators include glass, plastic, ceramic, polymeric materials, and porous membranes thereof among other separators known to those in the art.

Solid-state and gel-state positive electrodes of this invention can be used in solid-state or liquid format batteries, depending on the specific format of the electrolyte separator and negative electrode. Regardless of the format of the batteries using the positive electrode of this invention, the negative electrode can comprise any metal, any mixture of metals, carbon or metal/carbon material capable of functioning as a negative electrode in combination with the active-sulfur-based composite positive electrode of this invention. Accordingly, negative electrodes comprising any of the alkali or alkaline earth metals or transition metals for example, (the polyether electrolytes are known to transport divalent ions such as $Zn^{++}$) in combination with the positive electrode of this invention are within the ambit of the invention, and particularly alloys containing lithium and/or sodium.

Preferred materials for said negative electrodes include Na, Li and mixtures of Na or Li with one or more additional alkali metals and/or alkaline earth metals. The surface of such negative electrodes can be modified to include a protective layer, such as that produced on the negative electrode by the action of additives, including organosulfur compounds, phosphates, iodides, nitrides, and fluorides, and/or an inert physical barrier conductive to the metal ions from the negative electrode, for example, lithium ions transport in lithium phosphate, or silicate glasses, or a combination of both.

Also preferred materials for said negative electrodes include carbon, carbon inserted with lithium or sodium, and mixtures of carbon with lithium or sodium. Here, the negative electrode is preferably carbon, carbon inserted with lithium or sodium, and/or a mixture of carbon with lithium or sodium. When the negative electrode is carbon, the positive electrode is in the fully discharged state, comprising lithium or sodium sulfides and polysulfides. Particularly preferred negative electrodes for batteries are lithium inserted within highly disordered carbons, such as, poly p-phenylene based carbon, graphite intercalation compounds, and $Li_yC_6$ wherein y=0.3 to 2, for example, $LiC_6$, $Li_2C_6$ and $LiC_{12}$. When the negative electrode is carbon, the cells are preferably assembled with the positive electrode in the fully discharged state comprising lithium or sodium sulfides and/or polysulfides. The use of negative electrodes of the carbon, carbon inserted with lithium or sodium, and mixtures of carbon with lithium or sodium with the solid-state and gel-state positive electrodes of this invention are especially advantageous when the battery is in the liquid format.

Positive Electrode

The active-sulfur of the novel positive electrodes of this invention is preferably uniformly dispersed in a composite matrix, for example, the active-sulfur can be mixed with a polymer electrolyte (ionically conductive), preferably a polyalkylene oxide, such as polyethylene oxide (PEO) in which an appropriate salt may be added, and an electronically conductive material. Furthermore, the ionically conductive material may be in a solid-state, a gel-state, or a liquid-state format. In most cases it will be necessary or desirable to include a suitable polymeric electrolyte, for rapid ion transport within the electrode as is done with intercalation materials based electrodes. Furthermore, because the active-sulfur is not electrically conductive, it is important to disperse some amount of an electronically conductive material in the composite electrode.

Preferred weight percentages of the major components of the active-sulfur-based positive electrodes of this invention in a theoretically fully charged state are: from 20% to 80% active-sulfur; from 15% to 75% of the ionically conductive material (which may be gel-state or solid-state), such as an aprotic solvent or PEO with salt, and from 5% to 40% of an electronically conductive material, such as carbon black, electronically conductive polymer, such as polyaniline. More preferably, those percentages are: from 30% to 75% of active-sulfur; from 15% to 60% of the ionically conductive material; and from 10% to 30% of the electronically conductive material. Even more preferable percentages are: from 40% to 60% of active-sulfur; from 25% to 45% of the ionically conductive material; and from 15% to 25% of the electronically conductive material. Another preferred percentage by weight range for the electronically conductive material is from 16% to 24%.

Methods of Making a Positive Electrode:

An important feature of this invention is the ability to provide electrodes having active material (usually active-sulfur and/or a polydisulfide polymer) in intimate contact with both an ionic conductor and an electronic conductor. This facilitates ion and electron transport to and from the active material to allow nearly complete utilization of the active material. To this end, the invention provides a method of producing electrodes which ensures that at least about 5% of the active material in the resulting electrode will be available for electrochemical reaction. No prior method produces electrodes having such high availability of active-sulfur.

A preferred method of making electrodes in accordance with this invention is illustrated in the flow chart of FIG. 1. The method begins with a step 100 of combining the electrode components (including an electrochemically active material, an electronic conductor, and an ionic conductor). Next, at a step 102, the mixture is homogenized such that the electrode components are well mixed and free of agglomerates. Typically, a slurry will be formed by combining the electrode components with a liquid at either step 100 or step 102.

After the electrode components are homogenized and in slurry form, the slurry is coated on a substrate to form a thin film at a step 104. Best results will generally be obtained if the slurry is homogenized immediately before the film formation at step 104. This ensures that the slurry components have not settled or separated to any significant degree, thus providing a uniform film with the desired ratio of electrode components. Finally, at a step 106, the coated film is dried to form the electrode. The film preferably will be sufficiently thin to allow for rapid drying so that the electrode components do not significantly redistribute during drying step 106. The actual film thickness will, of course, depend upon the amount of liquid used in the slurry.

The components that are combined at step 100 include at least an electrochemically active insulator (e.g., elemental sulfur or a polydisulfide), an electronically conductive material, and an ionically conductive material. Appropriate ratios of these materials are presented above for the resulting electrodes. Generally the same ratios may be employed in the mixture used to make the electrodes. The electrochemically active insulator is preferably active-sulfur, but any electrochemically active insulator or moderately conductive material may benefit from the inventive method. The ionic conductor is, as noted, preferably a polymeric ion conductor such as a polyalkylene oxide, and more preferably PEO or amorphous PEO. However, it may also be a liquid or gel-state material. To increase the conductivity of the ion conductor, it typically will be provided with a salt containing the transported ion (e.g., a lithium salt such as lithium trifluoromethanesulfonimide or lithium perchlorate as described herein in connection with the electrolyte). The electronic conductor is preferably a carbon black or an electronically conductive polymer such as a polyaniline, polythiophene, polyacetylene, polypyrrole, etc. In an especially preferred embodiment, the electrochemically active material is active-sulfur, the ionic conductor is PEO (possibly with a small amount of an appropriate salt), and the electronic conductor is a carbon black.

In addition to the three above-mentioned "necessary" electrode components, other components that may be added to the mixture include (1) materials to catalyze the transfer of electrons from the electronically conductive material to the active material, (2) additives to protect an active metal electrode surface (e.g., lithium or sodium electrode surfaces) in cells that employ such electrodes, (3) dispersants, (4) binders, and (5) surfactants.

Materials that catalyze electron transport between the electrochemically active material and the electronic conductor are known in the art and include, for example, phthalocyanines, metallocenes, and brilliant yellow. Additives to protect an active metal electrode surface include, for example, organosulfur compounds such as poly-2,5-dimercapto-1,3,4-thiadiazole, phosphates, iodides, iodine, metal sulfides, nitrides, and fluorides. These materials are believed to provide a protective layer on the metal electrode surface. By casting them in the active-sulfur (or other insulator) electrode, small amounts of these protective agents will diffuse across the electrolyte to react with the metal electrode and provide the protective layer. Further, a dispersant (or dispersants) such as Brij or PEG may also be added to the mixture. Such materials reduce a tendency to agglomerate exhibited by some of the necessary components such as carbon black. Agglomeration, of course, degrades the quality of the resulting electrode by preventing thorough mixing of the components. Other additives are widely used in fabricating positive electrodes and are known in the art to have various benefits. The use of such additives in formation of electrodes is within the scope of this invention.

As noted, the components of the electrode mixture will typically be dispersed in a slurry. Various liquids may be employed in the slurry. Typically, but not necessarily, the liquid will not dissolve active-sulfur or carbon black. It may, however, dissolve polymeric components such as PEO or a polymeric electronic conductor. Preferred liquids evaporate quickly so that the resulting film dries completely and before redistribution of the components can occur. Examples of acceptable liquids for the slurry system include water, acetonitrile, methanol, ethanol, tetrahydrofuran, etc. Mixtures of liquid compounds may also be employed. In large-scale continuous processes, it may be desirable to use a relatively low volatility liquid such as water to facilitate liquid recovery for recycling.

The relative amounts of solid and liquid in the slurry will be governed by the viscosity required for subsequent processing. For example, electrodes formed by a tape casting apparatus may require a different viscosity slurry than electrodes formed with a Mayer rod. The slurry viscosity will, of course, be governed by such factors as the composition and amounts the slurry components, the slurry temperature, and the particle sizes in the slurry. When the mixture includes a soluble ionic conductor such as PEO, the slurry ratio is conventionally defined in terms of the amount of soluble material to liquid. Amounts of the remaining insoluble components are then pegged to the amount of soluble material. For PEO-containing electrodes, a preferred range of concentrations is between about 30 and 200 milliliters of solvent per gram of PEO.

The exact ordering in which components are added to the slurry is not critical to the invention. In fact, as illustrated in examples 18 to 20 below, various approaches have been found to work with this invention. In one embodiment, for example, the soluble components such as PEO and brij are first dissolved in the liquid solvent before the insoluble components are added. In another exemplary embodiment, all components except crystalline PEO are dispersed and dissolved before the crystalline PEO is added. The insoluble components may be added to the slurry sequentially or in a premixed form (i.e., the solid insolubles are mixed before addition to the slurry).

The process of homogenizing the electrode components (step 102 of FIG. 1) may take a variety of forms in accordance with the present invention. The process may vary depending upon whether electrode fabrication is performed batchwise or continuous. For small-scale batch operations, suitable slurry homogenization apparatus includes stir bars (preferably cross-type stir bars), paint mixers such as rotary blade mixers, paint shakers, and shear mixers. Further, any mixing apparatus conventionally used to make "slips" in the ceramic processing arts will be sufficient for use with this invention. By way of example, some other batch mixing systems employ ball milling, tumble mixing, shear mixing, etc. The amount of time required to obtain a suitably homogeneous mixture can be determined by routine experimentation with each of these pieces of mixing equipment.

Suitably homogeneous mixtures are evidenced by high availability of active electrode material in the resulting electrode. It has been found that with stir bars, homogenization typically requires about 2 days, whereas with paint mixers and paint shakers homogenization requires less time (on the order of a few hours). In scaling up agitators for suspending solid particles, the torque per unit volume generally should be kept constant. Even so, blending times typically are significantly longer in larger vessels than in smaller ones and this should be factored into any scale-up.

In large-scale and/or continuous electrode fabrication systems, an industrial agitator will generally be preferable. Design criteria for such systems are well known in the art and are discussed at, for example, pages 222–264 of McCabe and Smith "Unit Operations of Chemical Engineering" Third Edition, McGraw Hill Book Company, New York (1976), which reference is incorporated by reference herein for all purposes. Suitable systems include turbine agitators and axial-flow or radial-flow impellers in tanks or vessels with rounded bottoms. In general, the vessels should not have sharp corners or regions where fluid currents cannot easily penetrate. Further, the system should be designed to prevent circulatory currents which throw solid particles to the outside of the vessel where they move downward and concentrate. Circulatory currents can be mitigated by employing baffles in the system (e.g., vertical strips perpendicular to the wall of the vessel). Shrouded impellers and diffuser rings can also be used for this purpose.

Very soon after the slurry is homogenized, it is deposited as a film on a substrate (step 104 of FIG. 1). The exact amount of time between homogenization and deposition will depend upon the physical character of the slurry (viscosity, solids concentration, solids particle sizes, etc.). Significant settling and separation of the solids in the slurry is to be avoided. Settling can be slowed by employing (a) small particles of low density solids, (b) high concentrations of the solids, and/or (c) highly viscous liquids. Further the particles of the various solids components of the slurry can be chosen so that they all settle at about the same rate, thereby avoiding the problem of segregation. To the extent possible, the slurry, should be delivered to a substrate immediately after homogenization. For example, slip conditioning and supply systems such as these provided by EPH Associates, Inc. of Orem, Utah may be used to deliver slurry from a homogenizer directly to a substrate.

Preferably, the step of slurry film deposition does not rely on centrifugal, capillary or other forces that tend to exacerbate separation of the solid slurry components. Thus, for example, procedures involving dipping of a substrate into the slurry generally will not be suitable for use in the present invention.

Figure 2:
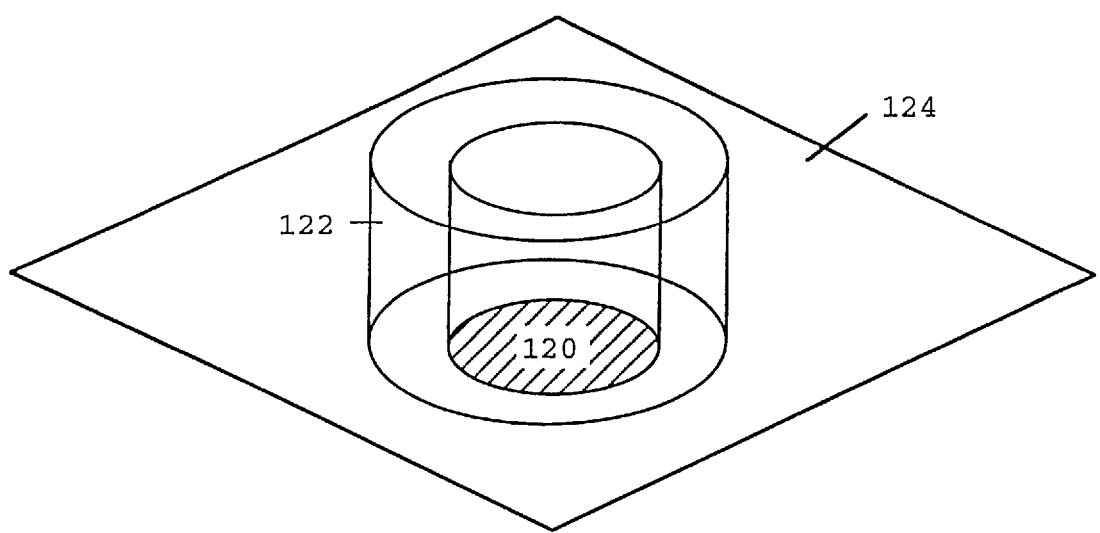
FIG. 2 illustrates a fixed tube apparatus for depositing a film of slurry on a substrate in accordance with one embodiment of this invention.

In accordance with this invention, preferred film formation procedures include (1) deposition onto a substrate via a fixed tube or structure temporarily defining a chamber above the substrate, (2) spreading via a Mayer rod, and (3) spreading via a doctor blade. Deposition via a fixed tube is illustrated in FIG. 2 where a tube 122 is placed against a substrate 124 with sufficient force to prevent slurry solids from leaking outside of deposition region 120. The tube 122 preferably is made from inert materials such as glass tube. It should have a smooth bottom so that it makes good contact and a reasonably impervious seal with substrate 124. An amount of slurry sufficient to cover region 120 is provided through the top of tube 122.

The slurry film also may be applied by spreading. In batch processes, a Mayer rod—which is rod of about ½ to 1 inch in diameter wound with thin wires—may profitably be used to roll out a thin layer of slurry film on the substrate. In continuous or batch processes, a doctor blade may be employed to deliver a thin layer of slurry to a moving sheet of substrate, as explained in more detail below.

Regardless of how the slurry film is applied, it should have a primary dimension, e.g., thickness, that allows for rapid drying. This thickness will, of course, depend upon such factors as slurry concentration and liquid volatility. In addition, the slurry film thickness should be chosen so as to produce electrodes of appropriate thickness for the ultimate battery application. For example, low power, high energy applications, such as batteries for pacemakers, may use thicker electrodes, e.g., up to a few millimeters. In contrast, high power applications, such as batteries for power tools or hybrid vehicles should employ thinner electrodes, e.g., no more than about 100 $\mu$m thick. It should be noted that electrodes of appropriate thickness for low power applications may be made by laminating two or more thinner electrodes. In this manner, the problem of slow drying associated with thick electrodes can be avoided.

Preferably the substrate on which the slurry is applied is a current collector such as a sheet of stainless steel, aluminum, copper, titanium, metallized PET, or other conductive material which will not react at operating cell conditions. Suitable current collectors may also take the form of expanded metals, screens, meshes, foams, etc. as is known in the art. In alternative embodiments, the substrate may be a sheet of inert material that does not adhere to dried electrode material. One such suitable substrate material is Teflon®. After the electrode film is dried, it is peeled away from such substrate and later contacted to a current collector such as one of the above-mentioned materials. Contacting to the current collector may be accomplished by hot pressing, crimping, etc. Alternatively, the current collector can be formed directly on the electrode material by a technique such as metal spraying, sputtering, or other technique known to those of skill in the art.

The process of forming an electrode concludes with a drying step (step 106 of FIG. 1). In batch processes, this is preferably accomplished in two steps: evaporation under ambient conditions for 30 seconds to 12 hours, followed by drying under vacuum for about 4 to 24 hours at room temperature or an elevated temperature. In continuous processes, drying may be accomplished by passing a sheet of electrode/substrate through a drying chamber such as an IR drier. A typical resulting active-sulfur electrode layer will have a density between about 0.0016 and 0.012 grams per $cm^2$.

It should be understood that if a liquid-state ionic conductor is employed, such ionic conductor may have to be added to the electrode after the drying step. The liquid ionic conductor may be introduced by simply contacting it with the dried electrode. In some cases, it may be helpful to draw the liquid into the electrode by applying vacuum.

Figure 3:
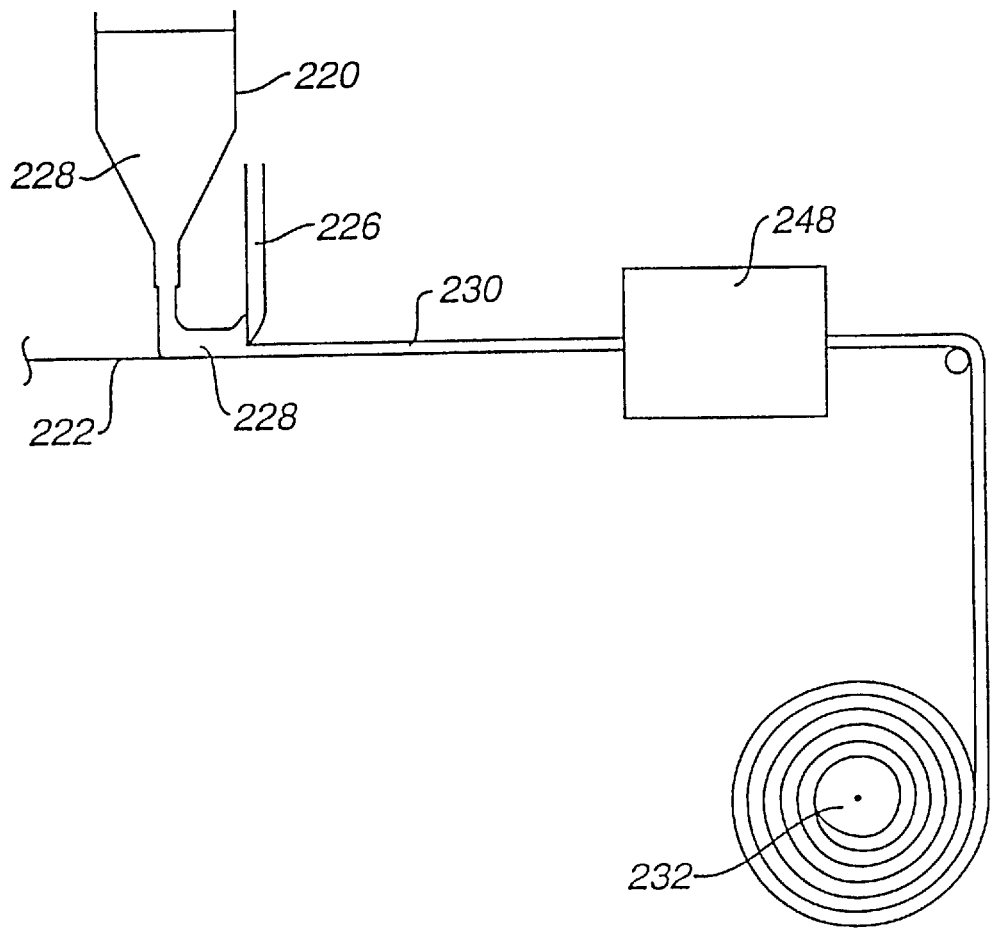
FIG. 3 illustrates apparatus for continuous slurry film deposition in accordance with one embodiment of this invention.

A continuous process for preparing sheets of precipitated polymer will now be described with reference to FIG. 3. As shown in FIG. 3, a hopper 220 dispenses a sheet of homogenized slurry 228 of suitable composition as described above. The slurry is deposited on a moving substrate sheet 222 which passes under blade 226 to produce a thin evenly spread layer of slurry 230 on substrate 222. The lower tip of blade 226 and the substrate 222 should be spaced such that slurry layer 230 has a thickness facilitating rapid drying as described above.

The substrate sheet 222—which moved along in the continuous process by a roller 232—may be made from a variety of suitable materials including flexible Teflon or any other release agent. In addition, the substrate may be a material that is intended to be incorporated in the ultimately produced electrode. For example, the substrate may include a metal foil, metallized PET, or screen that is to form a current collector in the final electrode. The substrate 222 with slurry layer 230 is directed into a drying apparatus 248 operated at a temperature sufficient to remove much of the liquid from the slurry. This apparatus may include one or more dryers such as IR dryers, and it may also have a condenser or other system (not shown) for recovering evaporated slurry liquid.

If the substrate sheet 222 is not a current collector, it may be separated from the electrode or partially dried electrode after the substrate enters drying apparatus 248. The separation can then be accomplished by providing separate uptake reels for substrate 222 (outside drying apparatus 248) and for the resulting electrode sheet. Of course, if the substrate 222 is a current collector or is otherwise intended to be part of the electrode, no separation is necessary, and the substrate/electrode laminate is taken up on reel 232 as shown.

In alternative embodiments, the electrode is formed without first preparing a slurry. Rather the electrode components—including the electrochemically-active insulator, the ion conductor, and the electron conductor—are homogenized in a solid state and formed into a sheet as by extrusion or calendaring. The solid state homogeneous mixture may also be coated onto a substrate by roll coating, blade coating, extrusion coating, curtain coating, or a related process. In each case, the solid state mixture is caused to flow by application of heat and/or pressure and the resulting viscous or viscoelastic mixture is passed though a die, a roller, or a blade. In such embodiments, the PEO or other polymeric components should be present in concentrations suitable to allow formation of a viscous or viscoelastic material under conditions encountered in standard polymer processing apparatus. Details of suitable polymer processing techniques are found in Middleman, "FUNDAMENTALS OF POLYMER PROCESSING", McGraw-Hill, Inc. 1977 which is incorporated herein by reference in its entirety and for all purposes. In addition to these processing techniques involving flow, alternative techniques within the scope of this invention include electrostatic deposition as by processes analogous to xerography. Further, dry processes conventionally used in the rubber processing arts may be applied to form electrodes in accordance with this invention. Because each of the above "dry" techniques do not involve a slurry, no drying step is required. Thus, there is less opportunity for the solid electrode components to segregate or agglomerate after homogenization.

Electrolyte Separators and Liquid Electrolytes

The electrolyte separator for solid-state format battery cells incorporating the positive electrode of this invention functions as a separator for the positive and negative electrodes and as a transport medium for the metal ions. As defined above, the material for such an electrolyte separator is preferably electronically insulating, ionically conductive and electrochemically stable.

When the battery cell is in a solid-state format, all components are either solid-state or gel-state and no component is in the liquid-state.

The aprotic organic liquids used in the electrolyte separators of this invention, as well as in the liquid electrolytes of this invention, are preferably of relatively low molecular weight, for example, less than 50,000 MW. Combinations of aprotic organic liquids may be used for the electrolyte separators and liquid electrolytes of the battery cells incorporating the positive electrode of this invention.

Preferred aprotic organic liquids of the battery cells incorporating the positive electrode of this invention include among other related aprotic organic liquids, sulfolane, dimethyl sulfone, dialkyl carbonates, tetrahydrofuran (THF), dioxolane, propylene carbonate (PC), ethylene carbonate (EC), dimethyl carbonate (DMC), butyrolactone, N-methylpyrrolidinone, tetramethylurea, glymes, ethers, crown ethers, dimethoxyethane (DME), and combinations of such liquids.

For the battery cells, incorporating the positive electrode of this invention, containing a liquid electrolyte wherein the negative electrode is carbon-containing, said liquid is also an aprotic organic liquid as described above. Such a format also preferably contains a separator within the liquid electrolyte as discussed above.

An exemplary solid-state electrolyte separator combined with this invention is a ceramic or glass electrolyte separator which contains essentially no liquid. Polymeric electrolytes, porous membranes, or combinations thereof are exemplary of the type of electrolyte separator to which an aprotic organic plasticizer liquid could be added according to this invention for the formation of a solid-state electrolyte separator containing less than 20% liquid.

Preferably the solid-state electrolyte separator is a solid ceramic or glass electrolyte and/or solid polymer electrolyte. Said solid-state ceramic electrolyte separator preferably comprises a beta alumina-type material, Nasicon or Lisicon glass or ceramic. The solid-state electrolyte separator may include sodium beta alumina or any suitable polymeric electrolyte, such as polyethers, polyimines, polythioethers, polyphosphazenes, polymer blends, and the like and mixtures and copolymers thereof in which an appropriate electrolyte salt has optionally been added. Preferred polyethers are polyalkylene oxides, more preferably, polyethylene oxide.

Exemplary but optional electrolyte salts for the battery cells incorporating the positive electrode of this invention include, for example, lithium trifluoromethanesulfonimide ($LiN(CF_3SO_2)_2$), lithium triflate ($LiCF_3SO_3$), lithium perchlorate ($LiClO_4$), $LiPF_6$, $LiBF_4$, $LiAsF_6$, as well as, corresponding salts depending on the choice of metal for the negative electrode, for example, the corresponding sodium salts. As indicated above, the electrolyte salt is optional for the battery cells of this invention, in that upon discharge of the battery, the metal sulfides or polysulfides formed can act as electrolyte salts, for example, $M_{x/z}S$ wherein x=0 to 2 and z is the valence of the metal.

Negative electrode

For solid-state battery cells incorporating the positive electrode of this invention, the negative electrode may comprise any metal, any mixture of metals, or any carbon or metal/carbon material capable of functioning as an active component of a negative electrode in combination with said active-sulfur positive electrode. For example, any of the alkali or alkaline earth metals or transition metals can be used, and particularly mixtures containing lithium and/or sodium.

Preferred materials for said negative electrode for the solid-state battery cell formats include sodium and/or lithium, and mixtures of sodium or lithium with one or more additional alkali metals and/or alkaline earth metals. Preferred materials for said negative electrode also include mixtures of sodium or lithium with one or more elements to form a binary or ternary alloy, such as, $Na_4Pb$, lithium-silicon and lithium-aluminum alloys.

A particularly preferred metal for a negative electrode is sodium, or at least a sodium base alloy (i.e., at least 90% by weight sodium) because of its low cost, low equivalent weight and its relatively low melting point of 97.8° C. However, other alkali metals such as Li or K, or mixtures of same with Na may also be used, as desired, to optimize the overall system.

Also preferred negative electrode materials for the solid-state battery cells incorporating the positive electrode of this invention include carbon, carbon inserted with lithium or sodium and/or a mixture of carbon with sodium or lithium. Exemplary and preferred are $Li_yC_6$ (wherein y=0.3 to 2), such as, $LiC_6$, negative electrodes which comprise graphite or petroleum coke, for example, graphite intercalation compounds (GICs), and carbon inserted within highly disordered carbons. The inserted carbon may also be that wherein some carbon has been alloyed with boron, or wherein the carbon has been prepared from low temperature pyrolysis (about 750° C.) of carbon or carbon-silicon containing polymers such that the carbon product retains some hydrogen or silicon or both. (See, Sato et al., "A Mechanism of Lithium Storage in Disordered Carbons," *Science*, 264: 556 (22 Apr., 1994), which discusses very good results with a preferred negative electrode of Li inserted within poly p-phenylene-based (PPP-based) carbon.)

For battery cells using the positive electrode of this invention that are in liquid formats, the negative electrode is carbon, carbon inserted with lithium or sodium, or mixtures of carbon and lithium or sodium as described above in relation to solid-state formats, including the preferable versions of such carbon-containing electrodes. For whatever format, if the negative electrode contains only carbon, the cell is in the theoretically fully discharged state, and the positive electrode comprises lithium or sodium sulfides or polysulfides.

Battery Cells

The battery cells containing the sulfur-based composite positive electrodes of this invention can be constructed according to conventional formats as described in the literature. For example, De Jonghe et al., U.S. Pat. No. 4,833,048 and Visco et al., U.S. Pat. No. 5,162,175. Such conventional formats are understood to be herein incorporated by reference.

The novel battery cells incorporating this invention, preferably secondary cells, more preferably thin film secondary cells, may be constructed by any of the well-known and conventional methods in the art. The negative electrode may be spaced from the positive sulfur electrode, and both electrodes may be in material contact with an ionically conductive electrolyte separator. Current collectors contact both the positive and negative electrodes in a conventional manner and permit an electrical current to be drawn by an external circuit.

Suitable battery constructions may be made according to the known art for assembling cell components and cells as desired, and any of the known configurations may be fabricated utilizing the invention. The exact structures will depend primarily upon the intended use of the battery unit.

A general scheme for the novel battery cells of this invention in a solid-state format may include a current collector in contact with the negative electrode and a current collector in contact with the positive electrode, and a solid-state electrolyte separator sandwiched between the negative and positive electrodes. In a typical cell, all of the components will be enclosed in an appropriate casing, for example, plastic, with only the current collectors extending beyond the casing. Thereby, reactive elements, such as sodium or lithium in the negative electrode, as well as other cell elements are protected.

The current collectors can be sheets of conductive material, such as, aluminum or stainless steel, which remain substantially unchanged during discharge and charge of the cell, and which provide current connections to the positive and negative electrodes of the cell. The positive electrode film may be attached to the current collector by directly casting onto the current collector or by pressing the electrode film onto the current collector. Positive electrode mixtures cast directly onto current collectors preferably have good adhesion. Positive electrode films can also be cast or pressed onto expanded metal sheets. Alternately, metal leads can be attached to the positive electrode film by crimp-sealing, metal spraying, sputtering or other techniques known to those skilled in the art. The sulfur-based positive electrode can be pressed together with the electrolyte separator sandwiched between the electrodes. In order to provide good electrical conductivity between the positive electrode and a metal container, an electronically conductive matrix of, for example, carbon or aluminum powders or fibers or metal mesh may be used.

A particularly preferred battery cell comprises a solid lithium or sodium electrode, a polymeric electrolyte separator, either solid-state or gel, preferably a polyalkylene oxide, such as, polyethylene oxide, and a thin-film composite positive electrode containing an elemental sulfur electrode (that is in the theoretically fully charged state), and carbon black, dispersed in a polymeric electrolyte. Optionally the electrolyte separator in such a preferred battery call can comprise an electrolyte salt.

Sulfur Electrodes having a Liquid Ionic Conductor

As mentioned, the battery cells of this invention may include a gel state or solid state electrolyte separator. In one preferred embodiment, the solid state separator is made from a polymeric material. These separators should be distinguished from ceramic electrolyte separators (which are also solid state separators) such as those employed in high temperature sodium-sulfur cells and related battery systems. The cells of this invention employing gel and polymeric solid state electrolyte separators have at least the following advantages: (1) an electrolyte that is flexible and easy to laminate with many different positive and negative electrodes, (2) an electrolyte that is compatible with many liquid and gel state ionic conductors used with positive electrodes of this invention, and (3) an electrolyte that is chemically well suited for transport of lithium ions and other cell discharge species.

In some embodiments of this invention, the positive electrode used with. a gel or polymeric solid state electrolyte separator includes at least a liquid ionic conductor, an electronic conductor, and active sulfur (e.g., elemental sulfur, a sulfide of the negative electrode metal, and/or one or more polysulfides of the negative electrode metal). The electronic conductor may be carbon or other material discussed above. Further, the positive electrode may be provided with one or more additives of the types discussed above.

Preferably, the ionic conductor is one or combinations of the following aprotic organic liquids or related compounds: sulfolane, dimethyl sulfone, dialkyl carbonates, tetrahydrofuran (THF), dioxolane, propylene carbonate (PC), ethylene carbonate (EC), dimethyl carbonate (DMC), butyrolactone, N-methylpyrrolidinone, tetramethylurea, glymes, ethers, crown ethers, and dimethoxyethane (DME). The liquid ionic conductor in the positive electrode may optionally include a salt such as one or more of the following: lithium trifluoromethanesulfonimide ($LiN(CF_3SO_2)_2$), lithium triflate ($LiCF_3SO_3$), lithium perchlorate ($LiClO_4$), $LiPF_6$, $LiBF_4$, $LiAsF_6$, as well as corresponding salts depending on the choice of metal for the negative electrode (e.g., sodium salts). It should be understood that such electrolyte salts are optional because the sulfur discharge products of this invention naturally increase the ionic conductivity of the liquid. Upon discharge of the battery, the metal sulfides or polysulfides formed can act as electrolyte salts.

In general, the positive electrode may include between from about 20% to 80% active-sulfur; from about 15% to 75% of the ionically conductive material, and from about 5% to 40% of an electronically conductive material, such as carbon black, electronically conductive polymer, such as polyaniline. More preferably, those percentages are: from about 30% to 75% of active-sulfur; from about 15% to 60% of the ionically conductive material; and from about 10% to 30% of the electronically conductive material. Even more preferable percentages are: from about 40% to 60% of active-sulfur; from 25% to 45% of the ionically conductive material; and from about 15% to 25% of the electronically conductive material. Another preferred percentage by weight range for the electronically conductive material is from about 16% to 24%.

In a cell including both a liquid ionic conductor (in the electrode) and a gel or polymeric solid state electrolyte separator as described, the positive electrode components may reside in a separate cell compartment defined on at least one side by the electrolyte separator. and on another side by a current collector such as a foil. Alternatively, the electrode may be defined by a carbon felt, a carbon paper, or other matrix of electronically conductive material. In such cases, the active sulfur may be interspersed throughout the matrix to facilitate charge transfer to and from the active sulfur.

It is important that the positive electrode be designed to make the active sulfur available to electronic and ionic charge carriers. This allows high utilization of the active sulfur in the cell. To this end, the electronic conductor in the positive electrode should form an interconnected matrix so that there is always a clear current path from the positive current collector to any position in the electronic conductor. The interconnected matrix of the electronic conductor should also be sufficiently "open" that there is room for precipitated electroactive species to deposit on the matrix. Suitable electronic conductors may be fibrous materials such as a felt or paper. Examples of suitable materials include a carbon paper from Lydall Technical Papers Corporation of Rochester, N.H. and a graphite felt available from Electrosynthesis Company of Lancaster, N.Y.

Any binder employed in the positive electrode should not prevent contact between the electronic conductor and the electroactive species. For example, the binder should not provide so much wetting that precipitated sulfur particles and/or the current collector are completely wetted and therefore unable to exchange electrons.

Specific examples of suitable polymeric solid state electrolyte separators include polyethers, polyimines, polythioethers, polyphosphazenes, and the like, as well as copolymers thereof and polymer blends. Preferably, an appropriate electrolyte salt is added to enhance conductivity. In a particularly preferred embodiment, the polymer separator is a polyalkylene oxide such as polyethyleneoxide. Specific examples of suitable gel state electrolyte separators include gelled aprotic solvents such as gelled versions of the aprotic solvents listed as appropriate ionic conductors for the positive electrode. For example, a gel state electrolyte separator of this invention may include a gelling agent in combination with at least one of sulfolane, dimethyl sulfone, a dialkyl carbonate, tetrahydrofuran, dioxolane, propylene carbonate, ethylene carbonate, dimethyl carbonate, butyrolactone, N-methylpyrrolidinone, tetramethylurea, glymes, ethers, a crown ether, and dimethoxyethane.

Preferably, liquid ionic conductor cells as described are secondary cells having high sulfur utilizations. Unlike primary cells which discharge only once, the secondary cells of this invention cycle between discharge and charge at least two times. Preferably, secondary cells of this invention will cycle at least 50 times, with each cycle having a sulfur utilization (measured as a fraction of 1675 mAh/g sulfur output during the discharge phase of the cycle) of at least about 10%. More preferably, at least 50 cycles will have a minimum sulfur utilization of at least about 20% (most preferably at least about 30%). Alternatively, the secondary cells of this invention will cycle at least two times, with each cycle attaining at least 50% utilization of sulfur in the positive electrode.

As used herein, "utilization" assumes that if all elemental sulfur in an electrode is fully utilized, the electrode will produce 1675 mAh/g of sulfur. That is, 100% utilization corresponds to 1675 mAh/g of the sulfur in the cell, and 10% utilization corresponds to 167.5 mAh/g of sulfur in the cell.

Unlike traditional liquid electrolyte separator cells, the gel or solid state separator cells of this invention are configured to resist self-discharge. Such self-discharge results when chemical species in the positive electrode dissolve in the electrolyte and migrate to the negative electrode where they chemically react to become unusable for generation of electrical energy. Such self-discharge mechanisms can be countered in various ways. For example, the negative electrode can be provided with a protective film which blocks dissolved positive electrode species from reacting with the negative electrode. This protective layer should be conductive to lithium ions and help prevent the formation of lithium dendrites or "mossy" lithium on repeated cycling. It can be produced by the action of additives, including organosulfur compounds, phosphates, iodides, nitrides, and fluorides. The protective layer may also be preformed from an inert physical barrier conductive to the metal ions from the negative electrode. Examples of such preformed protective layers include lithium phosphate, lithium silicate glasses, polymers, or a combinations of these. In a particularly preferred embodiment, the protective layer is poly(1-trimethylsilyl-1-propyne) ("PTMSP").

Overcharge Protection

The Li/S system exhibits significant tolerance to overcharge, which may be attributed to an intrinsic overcharge mechanism. While not wishing to be bound by theory, it is believed that oxidized overcharge products produced in the positive electrode near or at the end of the charging cycle travel to the negative electrode and affect the surface of the lithium. These overcharge products are reactive with an negative electrode passivation layer which consists, in part or wholly, of less oxidized lithium sulfides. A reaction between the more oxidized overcharge products and the passivation layer compounds reduces the overcharge products. Reduced species may then travel to the positive electrode where they may be reoxidized before returning to the negative electrode. Thus, it appears that a redox shuttle mechanism that gradually removes or reduces the thickness of the negative electrode passivating layer protects the battery from overcharge.

Regarding the species involved in the protective redox shuttle, it is believed that the more oxidized overcharge products from the positive electrode include lithium sulfides such as $Li_2S_x$, in which x>3 but probably 6<x<20. The reactivity of the sulfides depends on the value of x in $Li_2S_x$, with the reactivity increasing significantly when x>6. During overcharge, the reactive oxidized positive electrode products (e.g., those products having a value of x that is greater than 6) which are soluble in the electrolyte travel to the negative electrode where they are rapidly reduced by less oxidized species such as $Li_2S$ from the passivation layer. The more stable reduced products (e.g., those products having a value of x that is less than 6), then travel back to the positive electrode where they may be oxidized to the more reactive species in a continuation of the described redox cycle. This sulfide redox shuttle mechanism is therefore intrinsic to Li/S cells in which $Li_2S_x$ is soluble to some extent in the electrolyte.

Because the less oxidized species are more stable, the cells remain stably charged with, at least, x>6 reducing the self discharge rate to a low level.

The above described mechanism should be contrasted with conventional overcharge protection schemes in which a parasitic additive is provided to the cell. Such additives are chosen based upon characteristic voltages at which they are oxidized and reduced. The protection mechanisms of the present invention are, in contrast, based upon a composition rather than voltage. Only after all sulfur species are sufficiently oxidized (e.g., with x being approximately 5 or greater), will the overcharge mechanism of this invention be activated.

The invention's improvement over conventional overcharge protection mechanisms can be understood by considering how such mechanisms operate. By using a conventional additive in a cell, the cell voltage is maintained below a characteristic voltage. Thus, if the cell is overcharged or very rapidly charged, the cell voltage is maintained at a presumably safe level by the reaction of the additive.

As an example, consider the ferrocene compounds that are widely used as overcharge protecting additives. A given ferrocene may be oxidized at a voltage of about 3 volts (versus the lithium negative electrode). When during charge all positive electrode material has been fully charged, the cell voltage may approach 3 volts. If the ferrocene is present, it will react at this point. Specifically, it will be oxidized at the positive electrode, travel to the negative, be reduced there, and shuttle back to the positive electrode. This shuttle redox mechanism will protect the cell from attaining too high a voltage.

However, sometimes during rapid charging the cell voltage may slightly exceed the point at which the additive reacts, even though the cell has not been charged to full capacity. Then the charging current will be shunted to the ferrocene redox reaction and beneficial charging of the cell will cease until the cell voltage is lowered to the level where the ferrocene no longer reacts. This problem will not arise in the composition dependent mechanism of the present invention. As long as there is additional active-sulfur in a limited oxidation state, the charging reaction will proceed—regardless of cell voltages slightly exceeding the normal fully charged cell voltage.

It should be understood that the above-described overcharge protection system should work with many different cells employing a sulfur electrode (not just the above-described Li/Sulfur cells). In fact, most alkali metal-sulfur cells, alkaline earth metal-sulfur cells, and other metal-sulfur cells which have produced passivation layers and overcharge products that can be expected to interact via a redox shuttle similar to that described above specifically for the lithium-sulfur system. Such cells might include sodium-sulfur cells, potassium-sulfur cells, magnesium-sulfur cells, aluminum-sulfur cells, calcium-sulfur cells, etc. Of course, alloys of the alkali and alkaline earth metals may also be employed as the negative electrodes in these alkali metal-sulfur cells. Such alloys include those described above (e.g., lithium-magnesium alloys, lithium-aluminum alloys, lithium-lead alloys, sodium-aluminum alloys, sodium-lead alloys, sodium-silicon alloys, and the like).

To the extent that the sulfur electrodes of this invention are used with alkali metal intercalation negative electrodes (i.e., carbon-alkali metal electrodes), the systems may benefit from selective separators in which sulfides are insoluble. In one example, such separators would be conductive only to $Li^+$ single ions. Alternatively, the separator may include two materials: a layer of less selective material as used in a conventional lithium metal cell together with a thin film of material conductive only to $Li^+$ single ions.

Figure 14A:
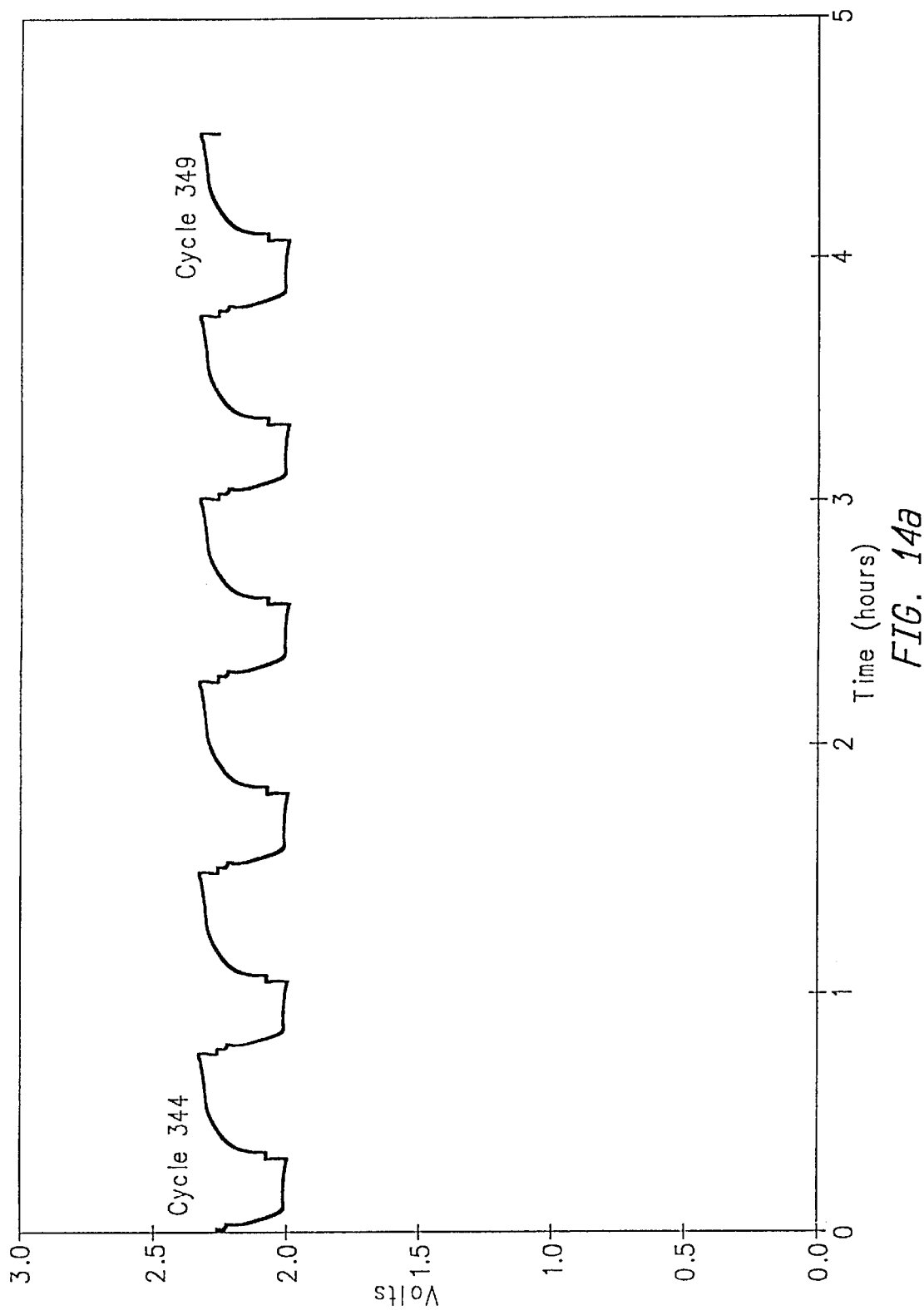
FIG. 14a is voltage vs. time cycling profile for a cell (discharged to a level of 200 mAh/gm active-sulfur and operated at 90° C.) that was consistently overcharged by 50% for each cycle.
Figure 14B:
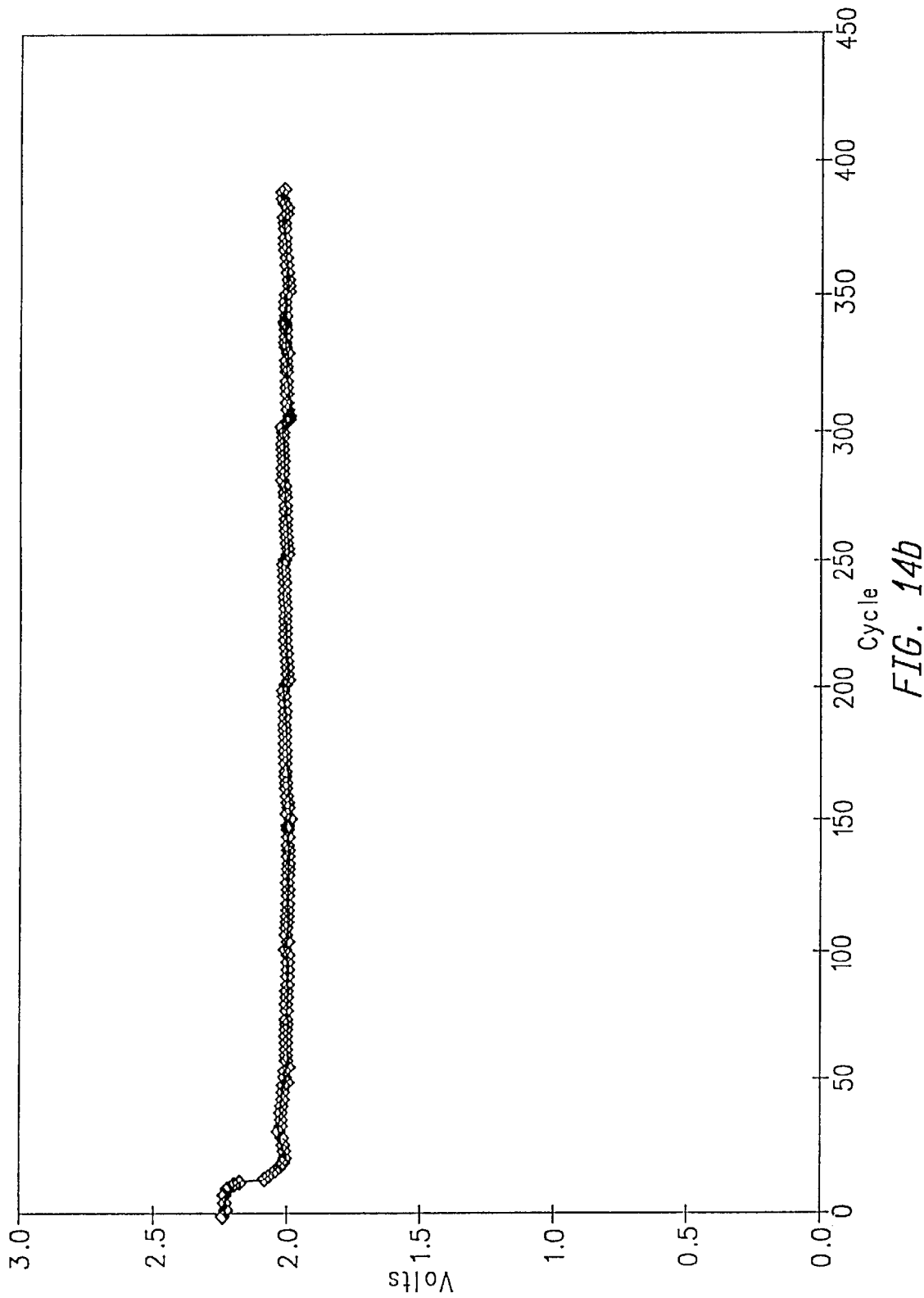

Preferably, the overcharge protection of this invention limits the cell voltage during overcharge to a safe level that does not substantially exceed the normal fully charged cell voltage. Thus, the overcharge voltage should remain below the level at which damage is done to cell components. For example, the overcharge voltage should not cause (i) the electrolyte to electrolyze, (ii) the current collectors to rapidly corrode, (iii) the cell separator to rapidly degrade, and (iv) the positive electrode to be irreversibly damaged. Preferably, the overcharge cell voltage will not exceed the normal fully charged cell voltage by more than about 4 volts, more preferably by not more than about 2 volts, and most preferably by not more than about 1 volt. In one specific embodiment, a lithium-sulfur cell having a fully charged normal cell voltage of at least about 2.2 volts had an overcharge cell voltage of not more than about 2.3 to 2.4 volts (see FIG. 14a described below).

It should be understood that the value of the "fully charged cell voltage" is not necessarily constant between any two metal-sulfur cells or is even constant for a given cell over that cell's life. Obviously, there will be some chemical and/or structural variations from cell to cell that will cause the fully charged cell voltage to vary. In addition, metal-sulfur cells sometimes exhibit gradual (or abrupt) changes in cell voltage over normal cycling. In all cases, the overcharge protection afforded by the present invention can be characterized as a limitation in the deviation from the value of the fully charged cell voltage.

Operating Temperatures

The operating temperature of the battery cells incorporating the novel positive electrode of this invention is preferably 180° C. or below. Preferred operating temperature ranges depend upon the application. Exemplary preferred operating temperature ranges include from –40° C. to 145° C.; from –20° C. to 145° C.; from –20° C. to 120° C.; and from 0° C. to 90° C. Most preferably for many applications, the cells incorporating this invention operate at ambient or above-ambient temperatures.

Different embodiments of this invention can provide different preferred operating temperature ranges. The choice of electrolyte can influence the preferred operating temperature ranges for the batteries incorporating the positive electrode of this invention. For example, when conventional PEO is used the preferred operating range is 60° C. to 120° C.; whereas when amorphous PEO (aPEO) is used, the battery can be run at room temperature, or in a range of 0° C. to 60° C.

Gel formats also provide for lower operating temperature ranges. Exemplary battery cells using the positive electrode of this invention containing, for example, polymeric electrolyte separators with increasingly greater percentage of a aprotic organic liquid immobilized by the presence of a gelling agent, can provide for increasingly lower operating temperature ranges. An exemplary operating temperature range for a solid-state battery having gel-state components of this invention would be from about –20° C. to about 60° C.

A battery with a liquid separator and an negative electrode comprising carbon, inserted carbon and/or a mixture of carbon and lithium or sodium can operate at a preferred temperature range of from –40° C. to 60° C.

The high temperature operating range of the battery cells based on the positive electrode of this invention can be limited by the melting point of either a solid electrode or a solid electrolyte. Thus sodium negative electrodes are limited to temperatures below 97.8° C., but sodium alloy electrodes, such as $Na_4Pb$, can be used in a solid form at well over 100° C.

The Li/S cell of this invention differs in several important aspects from the many high temperature sodium-sulfur cells such as those based on the Na/sulfur system first described by Kummer and Weber of the Ford Motor Company (U.S. Pat. Nos. 3,404,035 and 3,413,150). Most notably, the positive electrodes of such Na/S systems are not provided with a separate ion conductor such as the ion conductors described above. Further, in such Na/S systems, the positive electrodes consist of molten alkali polysulfides, requiring these cells to operate at temperatures above 250° C. The positive electrodes of such cells contain only molten sulfides and carbon. In addition, the high temperature of operation also makes the sodium negative electrode molten, thus requiring a ceramic electrolyte separator. Operation of such cells below 100° C. is not possible.

Specific Energy and Specific Power

The practical specific energies of the secondary cells utilizing this invention are preferably greater than 65 watthours per kilogram (Wh/kg), more preferably greater than 100 Wh/kg, still more preferably greater than 150 Wh/kg, even more preferably greater than 200 Wh/kg, and still even more preferably greater than 250 Wh/kg. While cells having specific energies in the above ranges are preferred for many applications, these ranges should not be viewed as limiting the invention. In fact, the cells of this invention can be expected to achieve specific energies in excess of 850 Wh/kg. Thus, for some applications, a preferred practical specific energy range of the batteries incorporating this invention is from about 100 Wh/kg to about 800 Wh/kg.

The practical steady-state specific power of the secondary cells utilizing this invention are preferably greater than 20 watts per kilogram (W/kg), more preferably greater than 50 W/kg, still more preferably greater than 100 W/kg, even more preferably greater than 150 W/kg, and still even more preferably greater than 250 W/kg. It is envisioned that with battery construction optimized for power, the steady-state power of this invention can exceed 750 W/kg. A preferred practical specific energy range of the batteries incorporating this invention is from about 50 W/kg to about 500 W/kg. The peak and pulse power performances would be many times greater than the steady-state power.

Cells made with lithium negative electrodes, solid-state or gel-state electrolyte separators, and positive electrodes made with elemental sulfur, polyethylene oxide (or modified polyethylene oxide) and carbon particles were constructed to test the performance of the batteries of this invention. Examples of these tests will serve to further illustrate the invention but are not meant to limit the scope of the invention in any way.

EXAMPLE 1

Solid-state cell: Cycling performance at an active-sulfur capacity of 330 mAh/gm for each recharge cycle evaluated at 30° C.

A positive electrode film was made by mixing 45% (percentage by weight) elemental sulfur, 16% carbon black, amorphous polyethylene oxide (aPEO) and lithium trifluoromethanesulfonimide (wherein the concentration of the electrolyte salt to PEO monomer units ($CH_2CH_2O$) per molecule of salt was 49:1), and 5% 2,5-dimercapto-1,3,4-dithiadiazole in a solution of acetonitrile (the solvent to PEO ratio being 60:1 by weight). The components were stir-mixed for approximately two days until the slurry was well mixed and uniform. A thin positive electrode film was cast directly onto stainless steel current collectors, and the solvent was allowed to evaporate at ambient temperatures. The resulting positive electrode film weighed approximately 0.0028 gm per cm$^2$.

The polymeric electrolyte separator was made by mixing aPEO with lithium trifluoromethanesulfonimide, (the concentration of the electrolyte salt to PEO monomer units ($CH_2CH_2O$) per molecule of salt being 39:1) in a solution of acetonitrile (the solvent to polyethylene oxide ratio being 15:1 by weight). The components were stir-mixed for two hours until the solution was uniform. Measured amounts of the separator slurry were cast into a retainer onto a release film, and the solvent was allowed to evaporate at ambient temperatures. The resulting electrolyte separator film weighed approximately 0.0144 gm per cm$^2$.

The positive electrode film and polymeric electrolyte separator were assembled under ambient conditions, and then vacuum dried overnight to remove moisture prior to being transferred into the argon glove box for final cell assembly with a 3 mil (75 micron) thick lithium negative electrode film (FMC/Lithco, 449 North Cox Road, Box 3925 Gastonia, N.C. 28054 (USA)).

Figure 4:
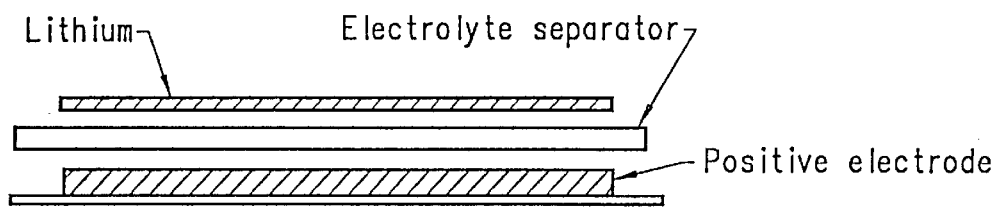
FIG. 4 provides a schematic of a Li/electrolyte separator/active-sulfur electrode cell of this invention.

A schematic of the cell layers are shown in FIG. 4. Once assembled, the cell was compressed at 2 psi and heated at 40° C. for approximately 6 hours. After heating the layers of lithium, electrolyte separator, and the positive electrode were well adhered.

The cell was then evaluated with a battery tester (Maccor Inc., 2805 West 40th Street, Tulsa, Okla. 74107 (USA)) inside the glove box at 30° C. That procedure was performed to eliminate any contamination problems of the lithium.

The cell was cycled to a constant capacity corresponding to delivering 330 mAh per gram of the active-sulfur in the positive electrode film. The rates used were 100–20 $\mu A/cm^2$ for discharging and 50–10 $\mu A/cm^2$ for charging to cutoff voltages of 1.8 and 3.0 volts, respectively.

Figure 5:
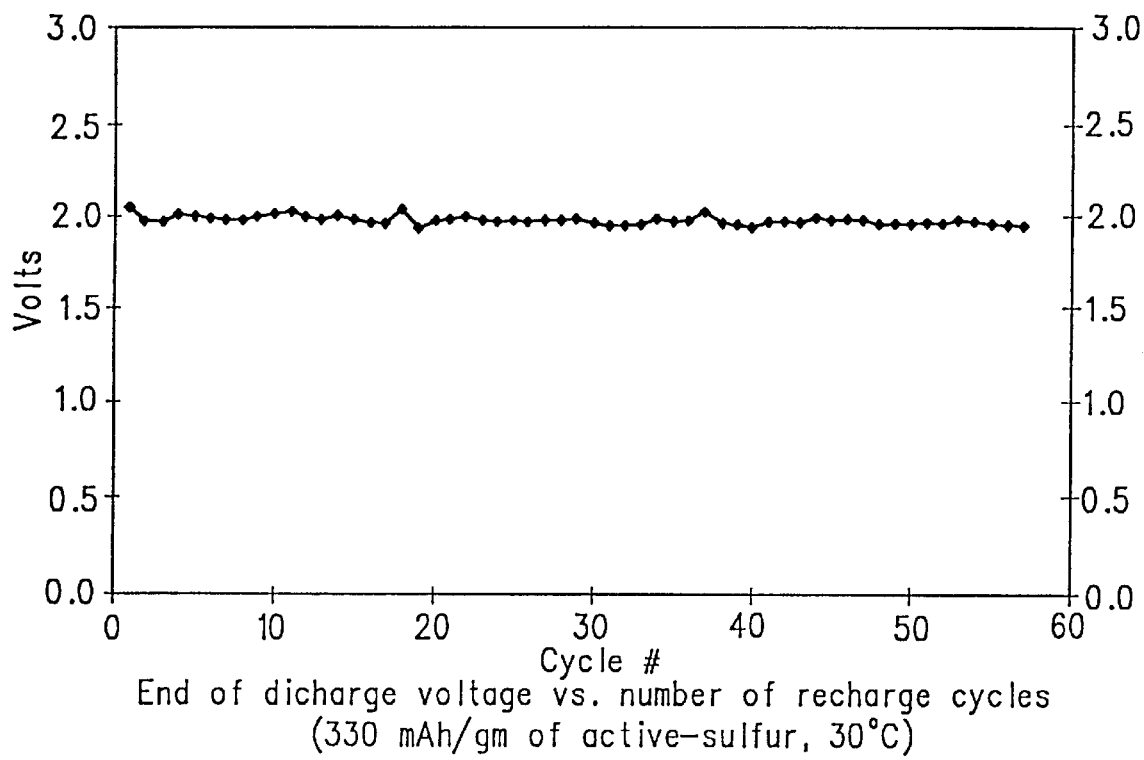
FIG. 5 illustrates the reversible cycling performance of a lithium cell (Li/amorphous PEO/active-sulfur) of this invention evaluated at 30° C. at an active-sulfur capacity of 330 mAh/gm for each cycle.

FIG. 5 shows the end of the discharge voltage of the cell after each recharge cycle. As evident from the graph, the cell performance is very consistent.

EXAMPLE 2

Solid-state cell: Total discharge capacity to 900 mAh/gm of active-sulfur evaluated at 30° C.

Figure 6:
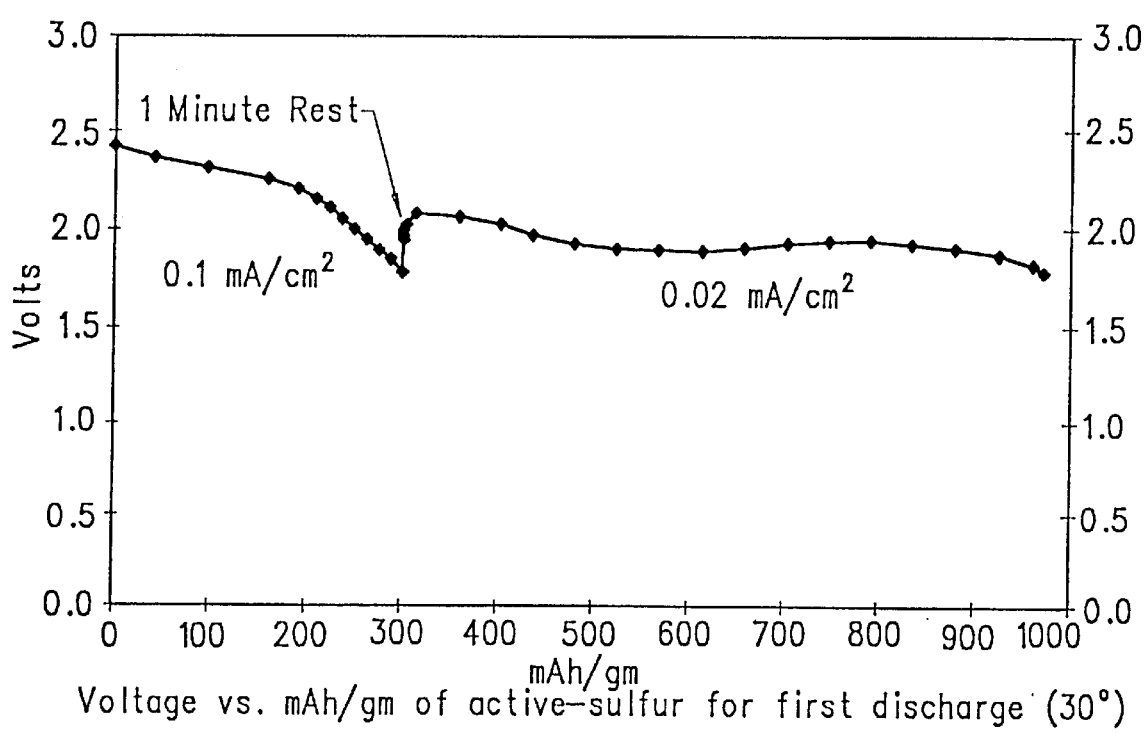
FIG. 6 illustrates the availability of the active-sulfur in the positive electrode of a lithium cell (Li/amorphous PEO/active-sulfur) of this invention evaluated at 30° C.

A cell identical to the one described in Example 1 was discharged to 1.8 volts at current densities of 100–20 $\mu A/cm^2$ at 30° C. to determine the total availability of the active-sulfur in the film. The resulting discharge curve is seen in FIG. 6. The total capacity delivered by this film was in excess of 900 mAh per gram of the active-sulfur, that is, a utilization of 54% of the available active-sulfur, wherein 100% would be 1675 mAh/gm.

EXAMPLE 3

Solid-state cell having gel-state components: Total discharge capacity to 900 mAh/gm of active-sulfur evaluated at 30° C.

A positive electrode film similar to the one described in Example 1 was made with a composition of 50% (percentage by weight) elemental sulfur, 16% carbon black, amorphous polyethylene oxide (aPEO) and lithium trifluoromethanesulfonimide (at a 49:1 concentration).

The electrolyte separator used was a gel made inside the glove box to avoid moisture and oxygen contamination. A starting solution consisting of 10% (weight percentage) of lithium trifluoromethanesulfonimide and 90% of tetraethylene glycol dimethylether (tetraglyme) was made. Then a solvent of 90% tetrahydrofuran (THF) was mixed with 10% of the starting solution. 5.6% Kynar Flex 2801 (Elf Atochem of North America, Inc., Fluoropolymers Department, 2000 Market Street, Philadelphia, Pa. 19103 (USA)), a gelling agent (PVDF), was added to the mixture.

The mixture was stirred for a few minutes and then left standing for 24 hours so that the components were absorbed into the Kynar,. The mixture was stirred again for a few minutes to homogenize the components and then heated for 1 hour at 60° C. Electrolyte separator films were cast onto a release film, and the THF solvent was allowed to evaporate at ambient temperatures. The resulting electrolyte separator film weighed approximately 0.0160 gm per cm$^2$.

Figure 7:
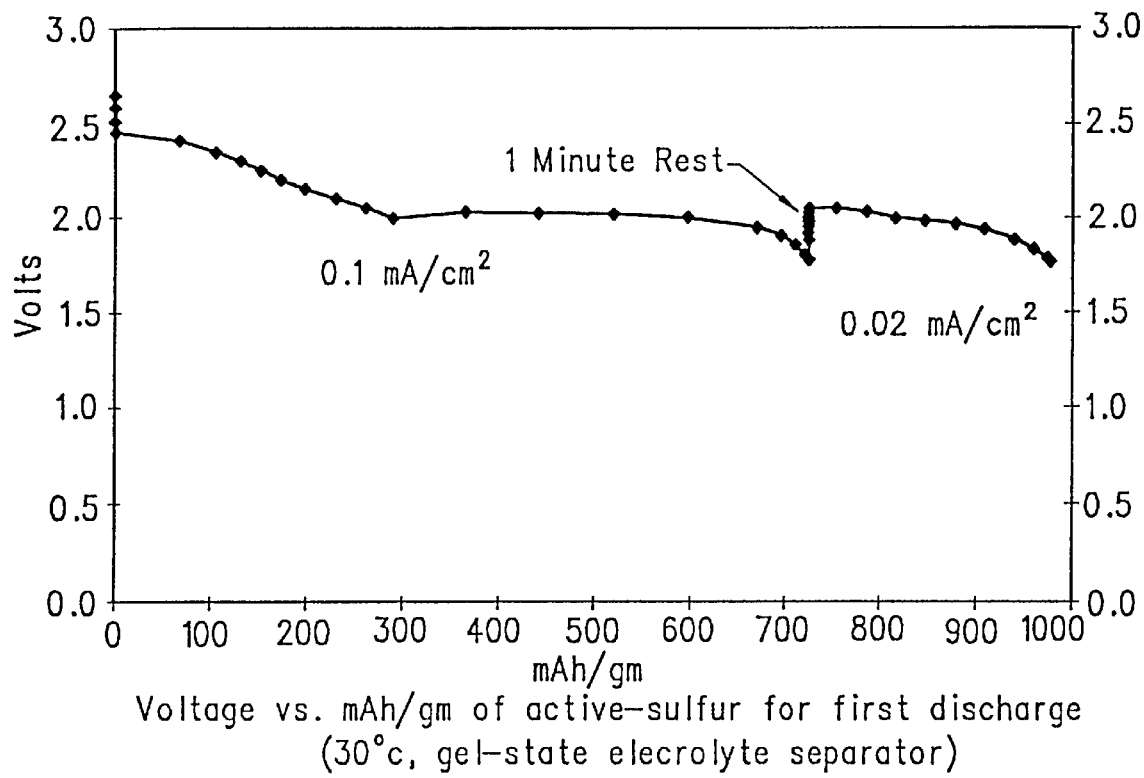
FIG. 7 illustrates the availability of the active-sulfur in the positive electrode of a lithium cell (Li/gel-state electrolyte separator/active-sulfur) of this invention evaluated at 30° C.

The resulting cell comprising the positive electrode film, the gel-state electrolyte separator film, and the lithium negative electrode was tested at the same conditions as the cell described in Example 2. The total capacity delivered by this film was also in excess of 900 mAh per gram of the active-sulfur, that is, a utilization of 54% of the available active-sulfur, wherein 100% would be 1675 mAh/gm as shown in FIG. 7.

EXAMPLE 4

Solid-state cell: Total discharge capacity to 1500 mAh/gm of sulfur evaluated at 90° C.

A positive electrode film similar to the one described in Example 1 was made for use at above ambient temperatures with a composition of 50% (weight percentage) elemental sulfur, 16% carbon black, polyethylene oxide (900,000 molecular weight) and lithium trifluoromethanesulfonirmide (a 49:1 concentration).

The solid-state electrolyte separator used was cast from a slurry of 900,000 MW PEO in acetonitrile without any additional electrolyte salts. The resulting electrolyte separator film weighed approximately 0.0048 gm per cm$^2$.

The cell was assembled as described in Example 1. Once assembled, the cell was compressed at 2 psi and heated at 90° C. for approximately 6 hours. The cell was tested at 90° C. inside a convection oven located in the glove box. The cell was discharged to 1.8 V at rates of 500 to 100 $\mu$A/cm$^2$.

Figure 8:
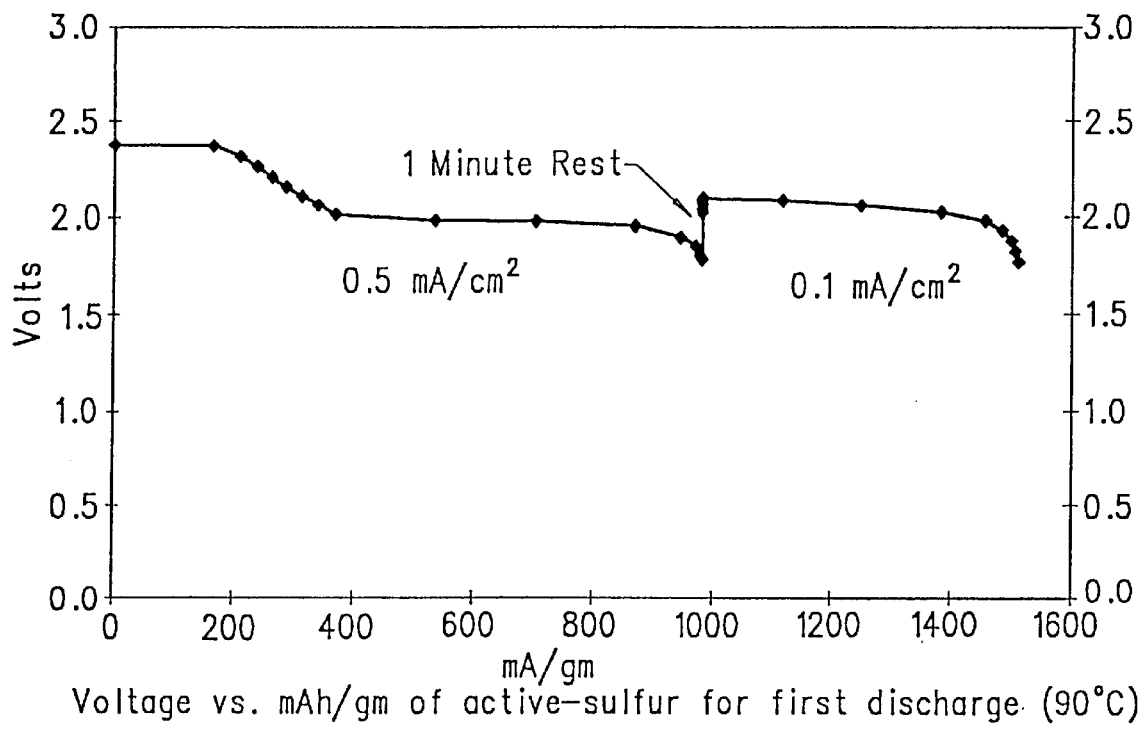
FIG. 8 illustrates the availability of the active-sulfur in the positive electrode of a lithium cell (Li/PEO/active-sulfur) of this invention evaluated at 90° C.

The capacity relative to the active-sulfur versus the voltage during discharge is shown in FIG. 8. The total capacity delivered by this film was also in excess of 1500 mAh per gram of the active-sulfur, that is, a utilization of 90% of the available active-sulfur, wherein 100% would be 1675 mAh/gm.

EXAMPLE 5

Solid-state cell: Cycling performance at a sulfur capacity of 400 mAh/gm for each cycle evaluated at 90° C.

A positive electrode film similar to the one described in Example 4 was made with a composition of 50% (weight percentage) elemental sulfur, 24% carbon black, polyethylene oxide (900,000 molecular weight) and lithium trifluoromethanesulfonimide (a 49:1 concentration). The electrolyte separator is also the same as described in Example 4. The cell was tested at 90° C. and cycled to a constant capacity corresponding to delivering 400 mAh/gm of the active-sulfur in the positive electrode film. The rate used was 500 $\mu$A/cm$^2$ for discharge to 1000–500 $\mu$A/cm$^2$ for charging at cutoff voltages of 1.8 and 2.6 volts, respectively.

Figure 9:
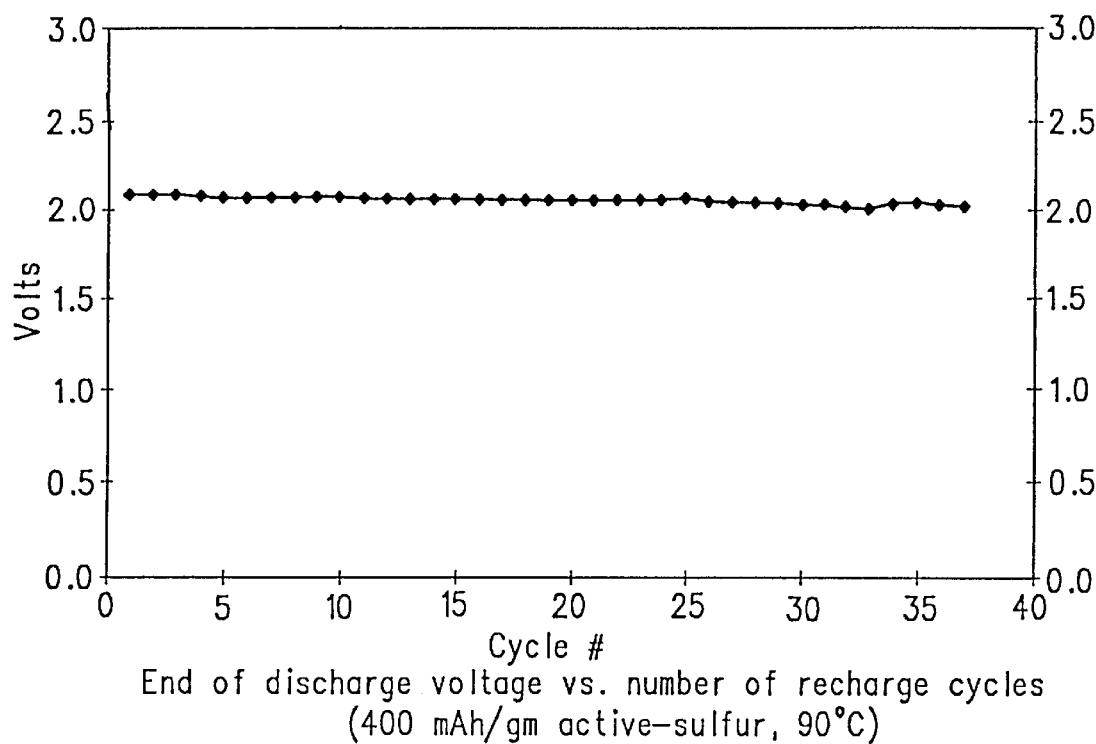
FIG. 9 illustrates the reversible cycling performance of a lithium cell (Li/PEO/active-sulfur) of this invention evaluated at 90° C. at an active-sulfur capacity of 400 mAh/gm for each cycle.

FIG. 9 shows the end of the discharge voltage of the cell after each recharge cycle. As evident from the graph, the cell performance is very consistent.

EXAMPLE 6

Solid-state cell: Cycling performance for each cycle to a cutoff voltage of 1.8 V evaluated at 90° C.

Figure 10:
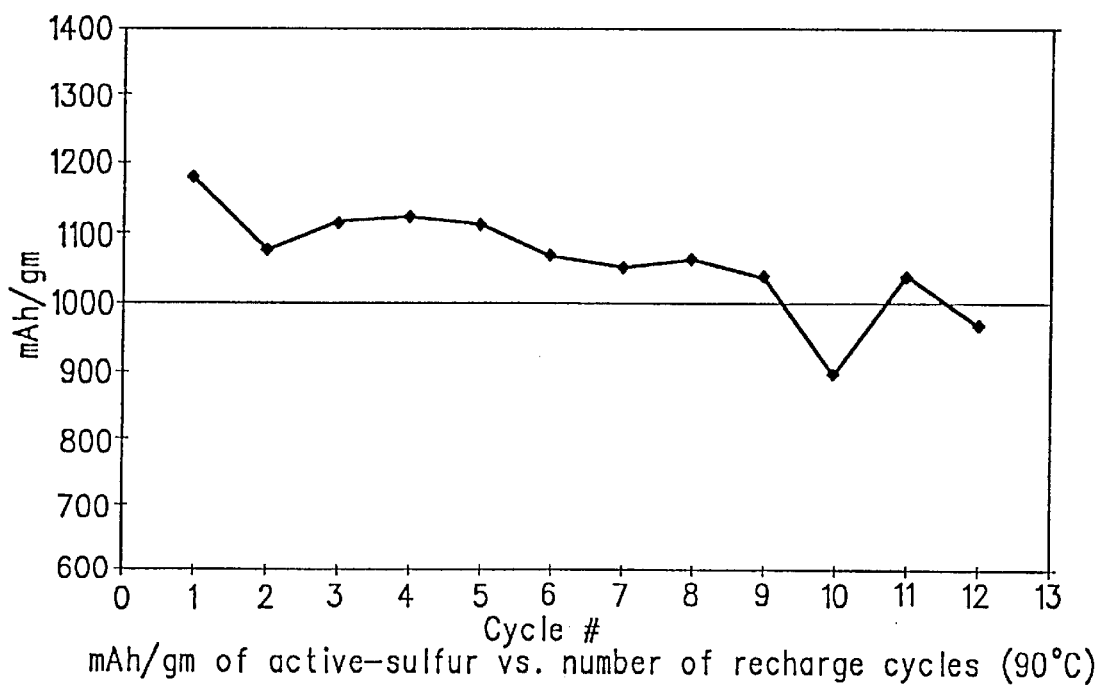
FIG. 10 illustrates the reversible cycling performance of a lithium cell (Li/PEO/active-sulfur) of this invention evaluated at 90° C.

A positive electrode film identical to the one described in Example 4 was made. The electrolyte separator is also the same as described in Example 4. The cell was tested at 90° C. and cycled between voltage limits between 1.8–2.6 volts. The rates used were 500–100 $\mu$A/cm$^2$ for charging. FIG. 10 shows the delivered capacity after each recharge. As evident from this graph most recharge cycles delivered above 1000 mAh per gram of the active-sulfur used in the positive electrode film.

EXAMPLE 7

Solid-state cell: Peak power performance evaluated at 90° C.

Figure 11:
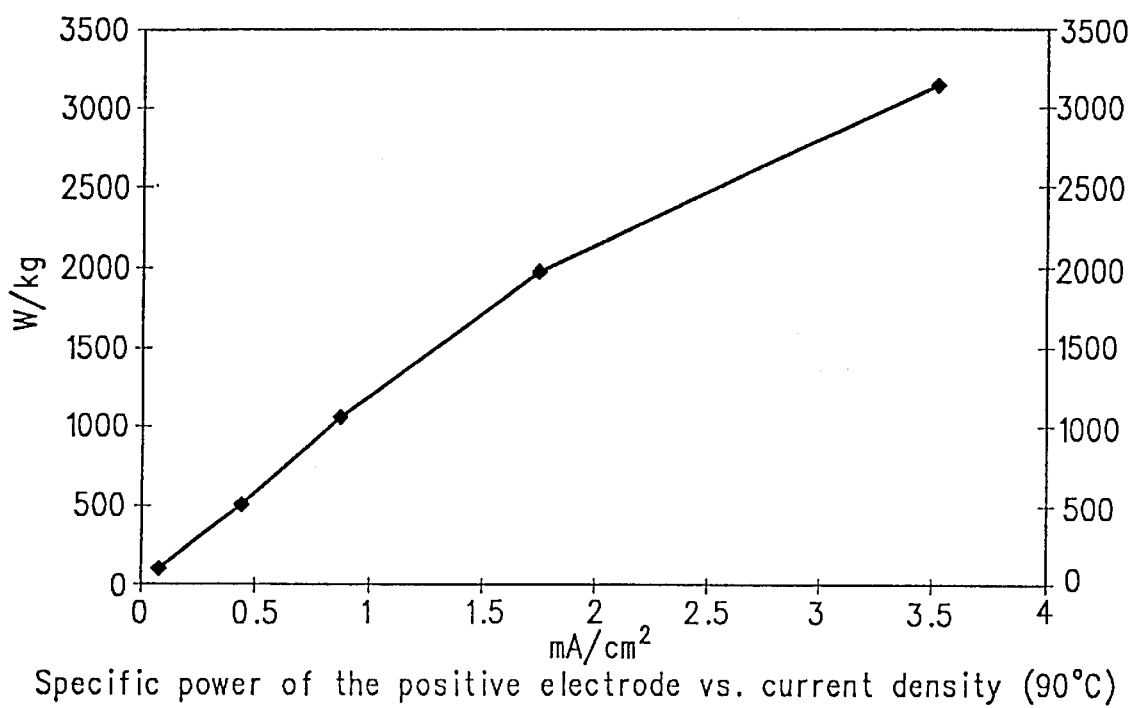
FIG. 11 illustrates the peak power performance of a lithium cell (Li/PEO/active-sulfur) of this invention evaluated at 90° C.

A positive electrode film similar to the one described in Example 4 was made with a composition of 50% (weight percentage) elemental sulfur, 16% carbon black, polyethylene oxide (900,000 molecular weight) and lithium trifluoromethanesulfonimide (a 49:1 concentration). The electrolyte separator is also the same as described in Example 4. The cell was tested at 90° C. and pulse discharged for a 30 second duration or to a cutoff voltage of 1.2 V. The discharge rates ranged from 0.1–3.5 mA/cm$^2$. The pulse power (W/kg) delivered by the positive electrode film versus the current density is shown in FIG. 11. As seen from the plot, an extraordinarily high pulse power of 3000 W/kg is capable of being attained.

EXAMPLE 8

A cell was tested under the conditions described in Example 5 above, except that the cell was cycled to a constant capacity corresponding to delivering 200 mAh/gm of the active-sulfur in the positive electrode film. The electrode was prepared from 50% elemental sulfur, 16% carbon, and the balance 900,000 MW PEO. A film of electrode material was formed with a Mayer rod onto a current collector. The separator was like the one in example 4 with 900,000 MW PEO and formed with a Mayer rod.

EXAMPLE 9

A cell was tested under the conditions described in Example 5 above, except that the cell was cycled to a constant capacity corresponding to delivering 300 mAh/gm of the active-sulfur in the positive electrode film. The electrode was prepared from 45% elemental sulfur, 16% carbon, 5% 2,5-dimercapto-1,3,4-dithiadiazole, and the balance 900,000 MW PEO. A film of electrode material was formed with a Mayer rod onto a current collector. The separator was like the one in example 4 with 900,000 MW PEO and formed with a Mayer rod.

EXAMPLE 10

A cell was tested under the conditions described in Example 5 above, except that the cell was cycled to a constant capacity corresponding to delivering 400 mAh/gm of the active-sulfur in the positive electrode film. The electrode was prepared from 45% elemental sulfur, 16% carbon, 5% 2,5-dimercapto-1,3,4-dithiadiazole, and the balance 900,000 MW PEO. A film of electrode material was formed with a Mayer rod onto a current collector. The separator was like the one in example 4 with 900,000 MW PEO and formed with a Mayer rod.

EXAMPLE 11

A cell was tested under the conditions described in Example 5 above, except that the cell was cycled to a constant capacity corresponding to delivering 600 mAh/gm of the active-sulfur in the positive electrode film. The electrode was prepared from 50% elemental sulfur, 24% carbon, 1% PbS, and the balance 900,000 MW PEO. A film of electrode material was directly cast onto a current collector. The separator was like the one in example 4 with 900,000 MW PEO and formed with a Mayer rod.

EXAMPLE 12

A cell was tested under the conditions described in Example 6 above. The electrode was prepared from 50% elemental sulfur, 16% carbon, and the balance 900,000 MW PEO. A film of electrode material was formed with a Mayer rod onto a current collector. The separator was like the one in example 4 but with the addition of 1% PbS.

EXAMPLE 13

A cell was tested under the conditions described in Example 6 above. The electrode was prepared from 50% elemental sulfur, 24% carbon, and the balance 900,000 MW PEO and lithium trifluoromethanesulfonimide (at a 49:1 weight ratio). A film of electrode material was formed with a Mayer rod onto a current collector. The separator was like the one in example 4 with 900,000 MW PEO and formed with a Mayer rod.

EXAMPLE 14

A cell was tested under the conditions described in Example 4 above, but at 70° C. The electrode was prepared from 50% elemental sulfur, 24% carbon, and the balance 900,000 MW PEO and lithium trifluoromethanesulfonimide (at a 49:1 weight ratio). A film of electrode material was formed with a Mayer rod onto a current collector. The separator was like the one in example 4 with 900,000 MW PEO and formed with a Mayer rod.

EXAMPLE 15

Figure 13:
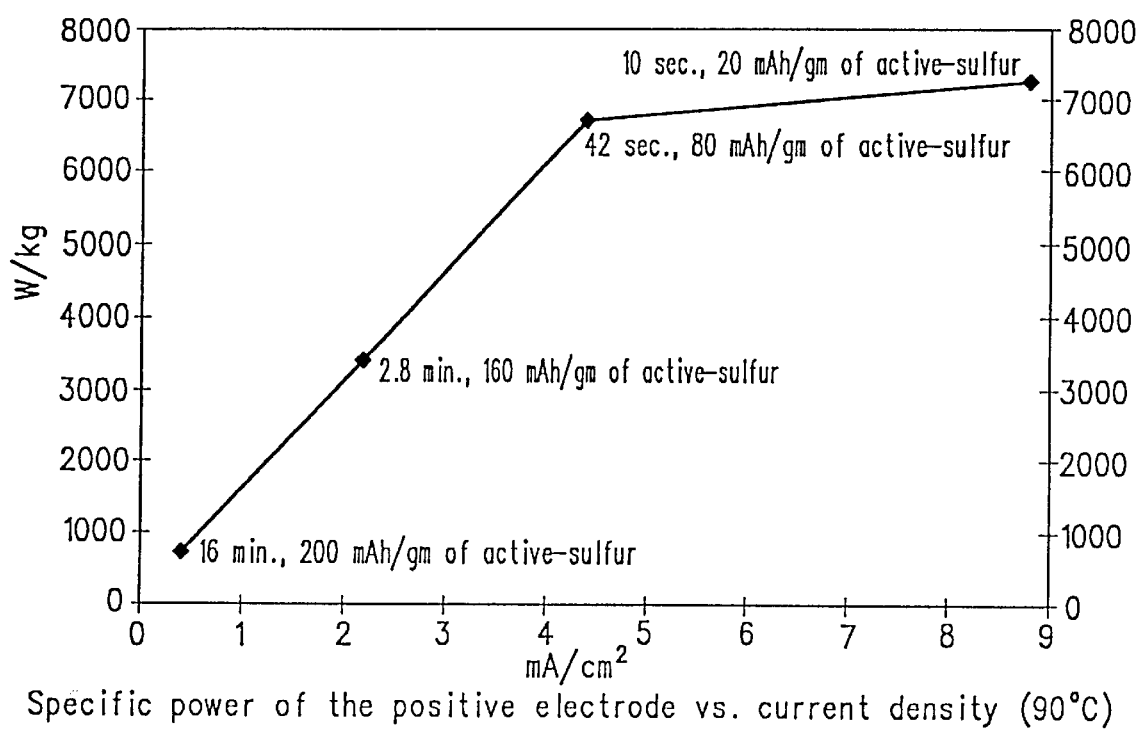
FIG. 13 illustrates the peak power performance of a lithium cell (Li/PEO/active-sulfur) of this invention evaluated at 90° C.

A cell was tested under the conditions described in example 7, but with discharge rates ranging from 0.4 to 9 mA/cm$^2$. The electrode was prepared with 50% elemental sulfur, 16% carbon, and the balance 900,000 MW PEO. A film of the electrode material was formed with a Mayer rod onto a current collector. The separator was like the one in example 4 with 900,000 MW PEO and formed with a Mayer rod. As seen from the plot presented in FIG. 13, an extraordinarily high pulse power of 7400 W/kg of the positive electrode can be attained.

Table 1 presented in FIG. 12a summarizes the performance of the representative battery cells of examples 1–7 under the specific testing conditions detailed in each example. Table 2 presented in FIG. 12b summarizes the performance of the representative battery cells of examples 8–14 under the specific testing conditions detailed in each example.

The demonstrated specific energies and specific powers listed above are based on the entire composite positive electrode. The electrolyte separators and lithium foils used for the laboratory tests were not optimized for the final battery. The battery projections are based on using 5 µm thick polymeric electrolyte separators, 30 µm thick lithium foil and 2.5–5.0 µm thick current collectors. Additionally, there is a 10% weight increase allocated for the external casing assuming for batteries larger than 1 Amphour.

Depending on the exact size and configuration of the cell laminate, the finished battery performance is approximately 30–70% of the positive electrode film performance. For simplicity, 50% has been used for the conversion between positive electrode performance and battery projections (this is equivalent to 100% battery burden). The calculated density range of the battery ranged from 1.0–1.6 gm/cm$^3$ depending on the specific components and configurations. For simplicity, a density of 1.25 gm/cm$^3$ is used to calculate the projected energy density (Wh/l).

As evident from the table, the battery systems containing the positive electrode of this invention demonstrate exceptionally high specific energies and exceed all now known solid-state intercalation compound-based batteries. The cells of this invention also outperform cells which operate at much higher temperatures such as the Na/beta"—alumina/ Na$_2$S$_x$ cell (350° C.), LiAl/LiCl, KCl/FeS$_2$ cell (450° C.).

It is seen that the invention provides high specific energy and power cells, the performance of which exceeds that of highly developed systems now known and in use. At the same time, the high energy and power are available at room temperature or ambient operation.

EXAMPLE 16

This example details one method of making active-sulfur electrodes of this invention. Initially, a three inch long piece of stainless steel (Brown Metals) was cut off of a four inch wide spool. Both sides of the sheet were then abraded with a sanding sponge to remove any insulating coating and ensure better electrical contact between the film and the stainless steel current collector. The abraded stainless steel current collector was wiped with acetone and Kim wipe EX-L until the Kim wipe was clean. A tab for electrically connecting the battery was made by cutting a section out of the stainless steel. The resulting stainless steel current collector was then weighed.

Next, the current collector was placed on a flat sheet of glass, and a standard 13 cm$^2$ glass casting ring was placed on the center of a 3"×3" portion of the steel current collector. Then a syringe was filled with a positive electrode slurry prepared according one of the examples above. Quickly 0.5 ml of the slurry was squirted out (or the desired volume to obtain the desired capacity per area) onto the area inside the glass ring. Before the solvent evaporated, the bead of slurry was spread so as to cover the area inside the glass ring with a wet film of even thickness. Thereafter, the film was allowed to dry for several hours before removing the glass ring from the current collector. An X-acto knife was used to cut the film off of the glass ring. The current collector with the film was again weighed in order to obtain the weight of the positive electrode film.

Electrodes were also prepared on Teledyne stainless steel or aluminum foils as described above but without abrading the steel or aluminum since there are no insulating coatings as on the Brown Metals steel.

EXAMPLE 17

A stainless steel current collector was prepared as described in example 15. The current collector was then placed on a smooth and flat glass sheet, and the middle of the Mayer rod ( # RDS 075 is standard now), was centered on the edge of the current collector. Several milliliters of slurry (as much as necessary so as to not run out of slurry) were poured in front of the rod. With one hand holding the substrate in place on the glass and the other holding the middle of the rod, the rod was dragged across the current collector leaving a wet film. The film was then dried and the process was repeated from the other end. The solvent content of the slurry was adjusted so that the wet film did not run (too much solvent) and did not have a ridged or raked appearance. When the film was dried, it was placed on a glass ring (at the center of the 3"×3" current collector), and a circular section was cut along the inside circumference of the ring. The excess film outside the circle was then scraped off and the weight of the film was determined.

EXAMPLE 18

Initially, an aluminum foil current collector prepared as in example 15 was placed on a sheet of glass, and taped to the ends of the glass so that it did not move while moving the Mayer rod. A Mayer Rod was placed on one end of the current collector and enough slurry to cover the desired area of current collector was squirted from a syringe in front of the Mayer Rod and onto the current collector. When the film was dry, the process was repeated as before but processed with a Mayer rod from a different end. When the film was dry, unwanted film was scraped off, and the current collector was trimmed to the desired area.

EXAMPLE 19

The following procedure was employed to prepare a positive electrode slurry having 50 wt % elemental sulfur, 16 wt % acetylene black, 2 wt % Brij 35, and 32 wt % 900,000 MW PEO. A 38×38 mm stir cross was placed in an 8 oz. Quorpac bottle (BWR Scientific, Brisbane, Calif.) with a Teflon lined top. To the bottle the following were added: 230 ml of acetonitrile. (Aldrich HPLC grade), 6 g of sublimed and ball milled sulfur powder (Aldrich), 1.93 g of acetylene (Shawinigin) carbon black (Chevron Cedar Bayou Plant), and 0.24 g of Brij 35 (Fluka). The contents of the bottle were then stirred overnight on a magnetic stir plate. The stir-plate power was set to stir at as high an RPM as possible without splattering or sucking air. The next day, as the slurry was rapidly stirring, 3.85 g of 900,000 MW PEO (Aldrich) was added in a stream so as not to form a few large lumps of solvent swollen PEO but rather many tiny lumps of solvent swollen PEO. During the next two days, the speed of the stir bar was adjusted to maintain as high as possible rpms, again without splattering or sucking air. After stirring for two nights, the PEO was dissolved and the slurry was used to prepare thin films by either ring casting or Mayer rod techniques.

Alternatively, sublimed and precipitated sulfurs were used instead of the ball milled sulfur described above, but instead of mixing for two nights, about two weeks of stirring were required. If the slurry is mixed for only two nights the resulting thin film was found to be porous and lumpy.

EXAMPLE 20

The following procedure was employed to prepare a positive electrode slurry having 50 wt % elemental sulfur, 24 wt % acetylene black, 2 wt % Brij 35, and the balance 900,000 MW PEO:lithium trifluoromethanesulfonimide (20:1) in acetonitrile (ml AN:gm PEO, 90:1). A 38×38 mm stir cross was placed in an 8 oz. Quorpac bottle (BWR Scientific, Brisbane, Calif.) with a Teflon lined top. To the bottle the following were added: 0.59 g lithium trifluoromethanesulfonimide (added in a dry box), 200 ml of acetonitrile (Aldrich HPLC grade), 5 g of sublimed and ball milled sulfur powder (Aldrich), 2.4 g of acetylene (Shawinigin) carbon black (Chevron Cedar Bayou Plant), and 0.2 g of Brij 35 (Fluka). The contents of the bottle were then stirred overnight on a magnetic stir plate. The stir-plate power was set to stir at as high an RPM as possible without splattering or sucking air. The next day, as the slurry was rapidly stirring, 1.8 g of 900,000 MW PEO (Aldrich) was added in a stream so as not to form a few large lumps of solvent swollen PEO but rather many tiny lumps of solvent swollen PEO. During the next two days, the speed of the stir bar was adjusted to maintain as high as possible rpms, again without splattering or sucking air. After stirring for two nights, the PEO was dissolved and the slurry was used to prepare thin films by either ring casting or Mayer rod techniques.

EXAMPLE 21

The following procedure was employed for various slurry compositions (identified below). Initially, a glass bottle and a stir bar were washed with acetone, and the stir bar was placed in the jar. Then an appropriate amount of acetonitrile (depending upon subsequent processing) was added to the jar and the bottle was capped. The bottle with its contents was placed onto a stir plate operated at sufficient power to create a vortex in the acetonitrile.

Next, PEO was measured and slowly added to the bottle while it was still on the stir plate. The PEO was introduced in very small amounts to maximize the contact with acetonitrile and promote rapid mixing. If salt was added, it was measured and added in the same fashion as the PEO. If there were other solubles (brij) to be added, they were also mixed in also at this point. All components were mixed until dissolved. Next, all insoluble materials including sulfur and carbon were measured and added to the mixture. Mixing was conducted for a minimum of two days.

The slurry combinations employed were as follows:
(A) 50 wt % elemental sulfur; 24% Carbon (Acetylene Black); 2% brij 35; 24% (20 moles PEO 900K to 1 mole lithium trifluoromethanesulfonimide) with 90 ml acetonitrile per gram of PEO.
(B) 50 wt % elemental sulfur; 16% Carbon (Acetylene Black); 1% brij 35; 33% PEO 900K with 60 ml acrylonitrile per gram of PEO.

Ranges of components used in preparing various compositions in accordance with this example are as follows: 24%–55% wt elemental sulfur; 8%–24% wt Carbon (Acetylene Black); 30 ml acrylonitrile per gram PEO to 110 ml acetonitrile per gram PEO; and 40, 60 and 90 ml water per gram PEO. Other compositions had various additives pegged to elemental sulfur according to the following: (1) 5 wt % Brilliant Yellow Dye additive with 55% elemental sulfur; (2) 5% 2,5-dimercapto-1,3,4-dithiadiazole with 45% elemental sulfur; (3) 2 wt % lithium iodide with 48% elemental sulfur; (4) 5 wt % iodine with 50% sulfur; (5) 1 wt % PbS with 49% elemental sulfur; and (6) 5 wt % polyethylene dithiol with 45% elemental sulfur.

The foregoing describes the instant invention and its presently preferred embodiments. Numerous modifications and variations in the practice of this invention are expected to occur to those skilled in the art. Such modifications and variations are encompassed within the following claims.

All references cited herein are incorporated by reference.

What is claimed is:

1. A battery cell comprising:
a) a negative electrode including a metal or an ion of the metal;
b) a positive electrode comprising
   i) an electrochemically active material comprising sulfur in the form of at least one of elemental sulfur, a sulfide of the metal, and a polysulfide of the metal, and
   ii) an electronically conductive material; and
c) a gel-state or polymeric solid-state electrolyte separator electronically separating the positive and negative electrodes,
d) wherein at least about 10% of the sulfur is accessible to electrons and ionic charge carriers.

2. The battery cell of claim 1, wherein the battery cell is rechargeable.

3. The battery cell of claim 2, wherein at least about 10% of this sulfur is accessible to electrons and ionic charge carriers over at least about 50 successive cycles.

4. The battery cell of claim 3, wherein at least about 50% of the sulfur is accessible to electrons and ionic charge carriers that over at least about 2 successive cycles.

5. The battery cell of claim 1, wherein the metal of the negative electrode includes at least one of sodium and lithium.

6. The battery cell of claim 5, wherein the metal in the negative electrode is a lithium metal electrode.

7. The battery cell of claim 1, wherein the negative electrode is a lithium intercalation electrode.

8. The battery cell of claim 1, wherein the electronic conductor of the positive electrode is at least one of carbon and an electronically conductive polymer.

9. The battery cell of claim 8, wherein the positive electrode further comprises an polymeric disulfide material in which the disulfide bond is located in the material's backbone.

10. The battery cell of claim 1, wherein the electrolyte separator comprises a gel-state electrolyte separator including at least 20% by weight of an aprotic organic liquid immobilized by the presence of a gelling agent.

11. The battery cell of claim 1, wherein the electrolyte separator comprises a polymeric solid-state electrolyte separator.

12. The battery cell of claim 11, wherein in the polymeric solid-state electrolyte separator comprises a polymer of ethylene oxide.

13. The battery cell of claim 1, wherein the positive electrode further comprises an ionic conductor.

14. The battery cell of claim 1, wherein the electrolyte separator comprises an aprotic organic liquid.

15. A battery cell comprising:
   a) a negative electrode including a metal or an ion of the metal;
   b) a positive electrode comprising
      i) an electrochemically active material comprising sulfur in the form of at least one of elemental sulfur, a sulfide of the metal, and a polysulfide of the metal,
      ii) an electronically conductive material, and
      iii) a liquid state ionic conductor, and
   c) a gel-state or polymeric solid-state electrolyte separator electronically separating the positive and negative electrodes,
   d) wherein at least about 10% of the sulfur is accessible to electrons and ionic charge carriers.

16. The battery cell of claim 15, wherein the battery cell is rechargeable.

17. The battery cell of claim 16, wherein at least about 10% of this sulfur is accessible to electrons and ionic charge carriers over at least about 50 successive cycles.

18. The battery cell of claim 17, wherein at least about 20% of the sulfur is accessible to electrons and ionic charge carriers that over at least about 50 successive cycles.

19. The battery cell of claim 18, wherein at least about 50% of the sulfur is accessible to electrons and ionic charge carriers that over at least about 2 successive cycles.

20. The battery cell of claim 15, wherein the metal of the negative electrode includes at least one of sodium and lithium.

21. The battery cell of claim 20, wherein the metal in the negative electrode is a lithium metal electrode.

22. The battery cell of claim 15, wherein the electronic conductor of the positive electrode is at least one of carbon and an electronically conductive polymer.

23. The battery cell of claim 22, wherein the positive electrode further comprises an organodisulfide material in which the disulfide bond is located in the materials backbone.

24. The battery cell of claim 15, wherein the electrolyte separator comprises a gel-state electrolyte separator including at least 20% by weight of an aprotic organic liquid immobilized by the presence of a gelling agent.

25. The battery cell of claim 15, wherein the electrolyte separator comprises a polymeric solid-state electrolyte separator.

26. The battery cell of claim 25, wherein in the polymeric solid-state electrolyte separator comprises a polymer of ethylene oxide.

27. The battery cell of claim 15, wherein the liquid state ionic conductor includes at least one of sulfolane, dimethyl sulfone, a dialkyl carbonate, tetrahydrofuran, dioxolane, propylene carbonate, ethylene carbonate, dimethyl carbonate, butyrolactone, N-methylpyrrolidinone, tetramethylurea, glymes, ethers, a crown ether, and dimethoxyethane.

28. The battery cell of claim 15, wherein the electrolyte separator includes a gelling agent and at least one of sulfolane, dimethyl sulfone, a dialkyl carbonate, tetrahydrofuran, dioxolane, propylene carbonate, ethylene carbonate, dimethyl carbonate, butyrolactone, N-methylpyrrolidinone, tetramethylurea, glymes, ethers, a crown ether, and dimethoxyethane.

* * * * *